(12) United States Patent
Zmiyiwsky et al.

(10) Patent No.: US 10,231,809 B2
(45) Date of Patent: Mar. 19, 2019

(54) DENTAL IMPLEMENT AND METHOD OF USING THE SAME

(71) Applicant: Zee Zee Corporation, Mississauga (CA)

(72) Inventors: Zenovia Zmiyiwsky, Mississauga (CA); Vera Zmiyiwsky, Mississauga (CA)

(73) Assignee: Zee Zee Corporation, Mississauga, Ontario (CA)

( * ) Notice: Subject to any disclaimer, the term of this patent is extended or adjusted under 35 U.S.C. 154(b) by 241 days.

(21) Appl. No.: 15/170,077

(22) Filed: Jun. 1, 2016

(65) Prior Publication Data

US 2016/0354187 A1 Dec. 8, 2016

Related U.S. Application Data

(60) Provisional application No. 62/170,229, filed on Jun. 3, 2015.

(51) Int. Cl.
*A61C 15/02* (2006.01)
*B08B 1/00* (2006.01)
*A46B 5/00* (2006.01)

(52) U.S. Cl.
CPC ............ *A61C 15/02* (2013.01); *A46B 5/0008* (2013.01); *A46B 5/0095* (2013.01); *B08B 1/002* (2013.01); *A46B 2200/108* (2013.01)

(58) Field of Classification Search
None
See application file for complete search history.

(56) References Cited

U.S. PATENT DOCUMENTS

| | | | | |
|---|---|---|---|---|
| 4,750,501 A | * | 6/1988 | Ackermann | ........... A45D 40/06 132/318 |
| 6,973,932 B2 | * | 12/2005 | Ko | ........................ A61C 15/00 132/309 |
| D703,955 S | * | 5/2014 | Nanda | ........................... D4/104 |

* cited by examiner

*Primary Examiner* — Eric W Golightly
(74) *Attorney, Agent, or Firm* — Sand, Sebolt & Wernow Co., LPA

(57) ABSTRACT

A dental implement for cleaning interproximal spaces and a method of use. The implement includes a sleeve with first and second ends and a bore defined therebetween. A stack of cartridges is insertable into the bore. Each cartridge includes a cleaning tip such as an interproximal brush. A cap may be engaged with the sleeve to protect the tip and keep it hygienic. The cartridges are progressively advanced along the bore to present their cleaning tip for use. A locking member secures the uppermost cartridge in place. Once used, a cartridge is removed from the sleeve and may be discarded or inserted into an opening to the bore in the sleeve's second end. The tip may be snapped off prior to insertion. The cartridge stack is drawn along the bore as the uppermost cartridge is removed or insertion of the spent cartridge will advance the cartridge stack along the bore.

19 Claims, 22 Drawing Sheets

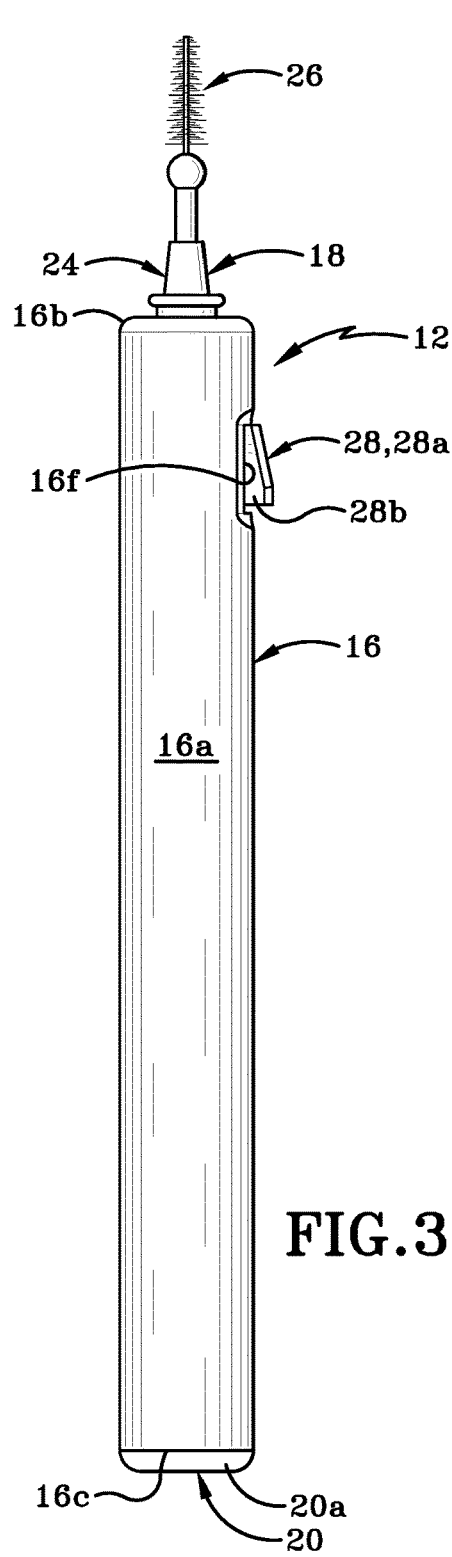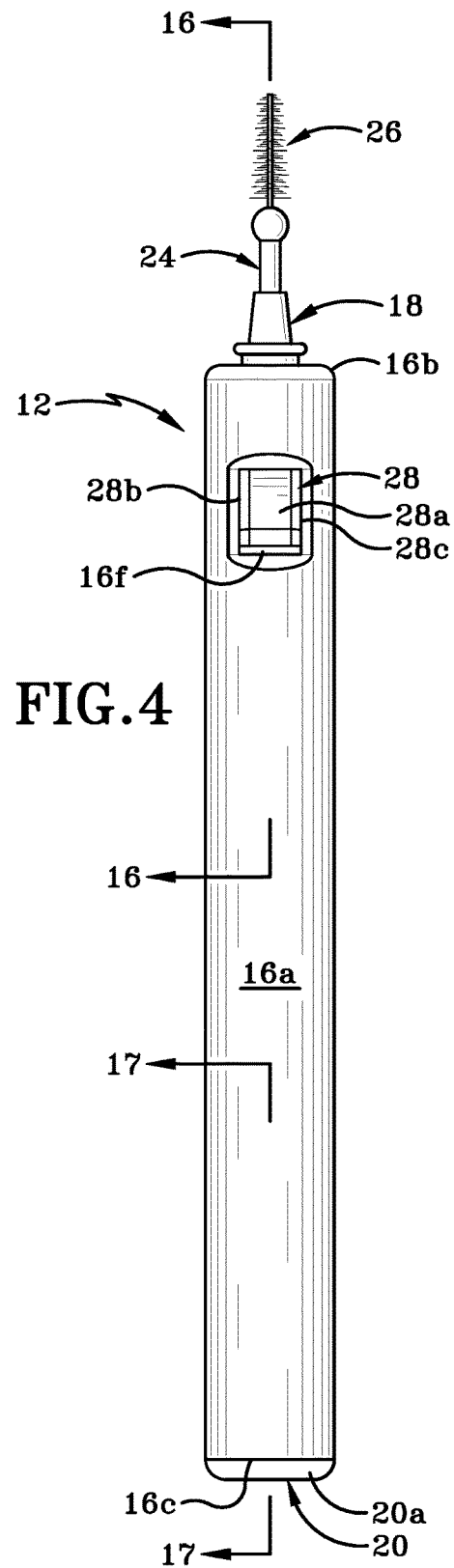

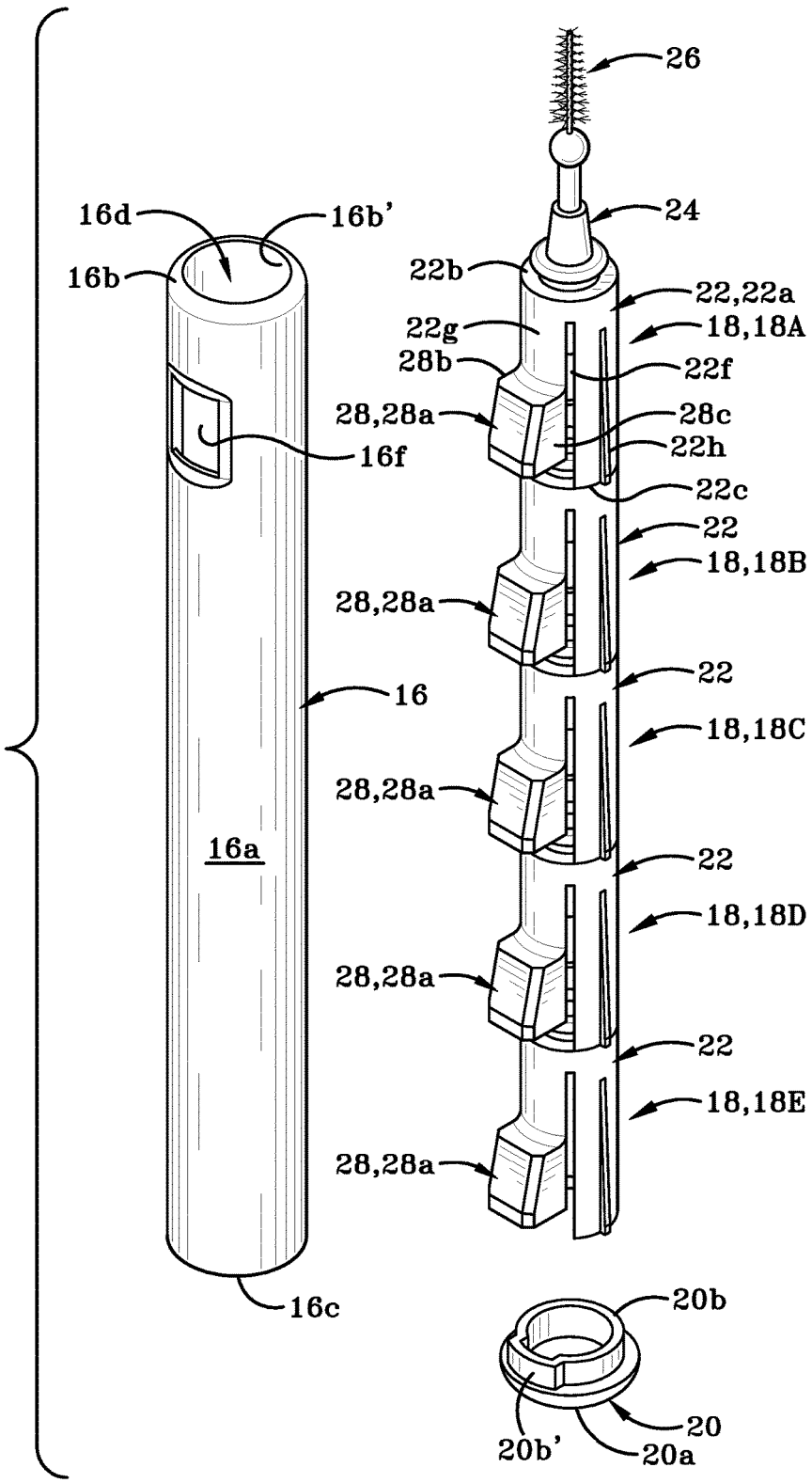

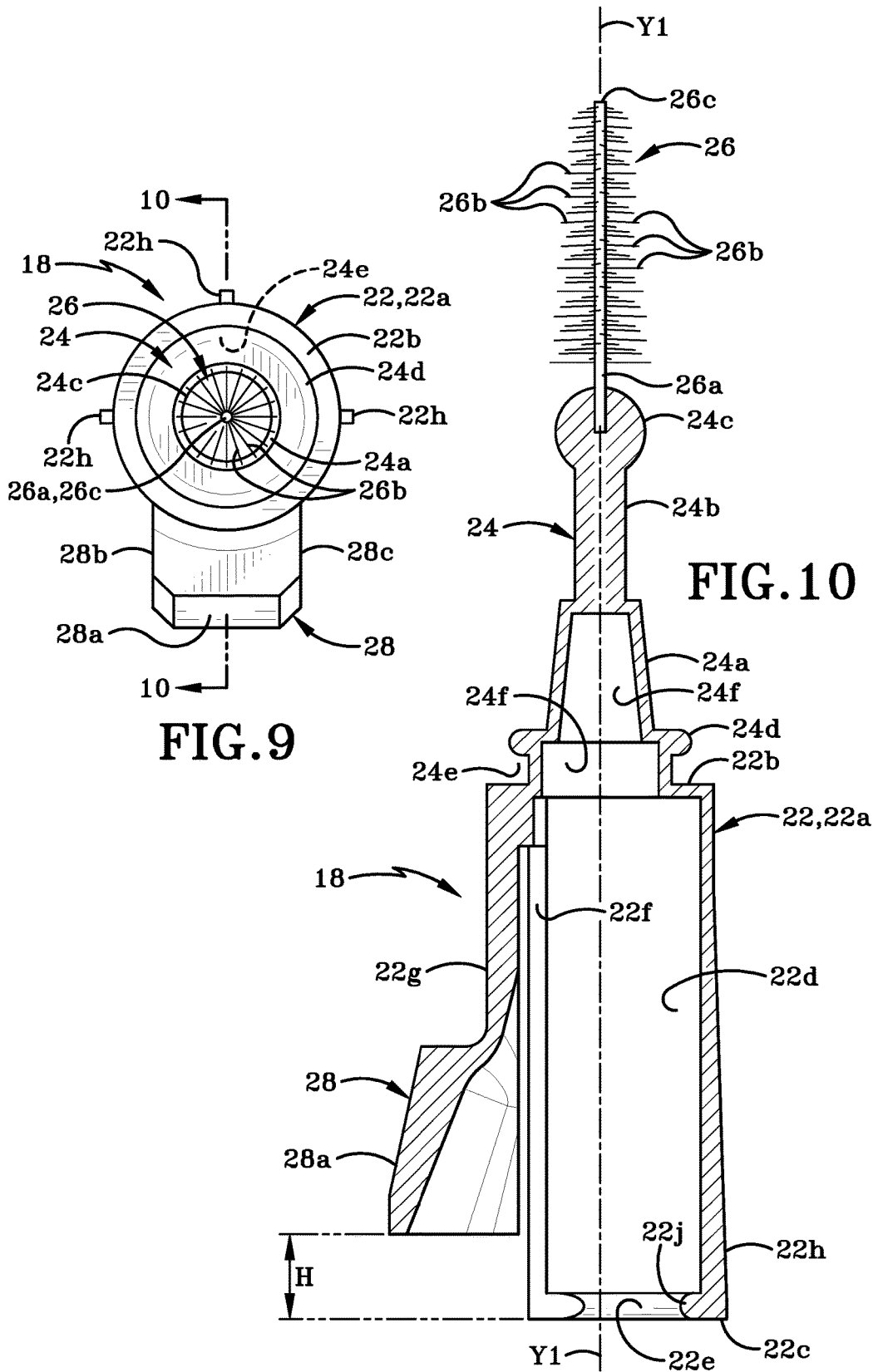

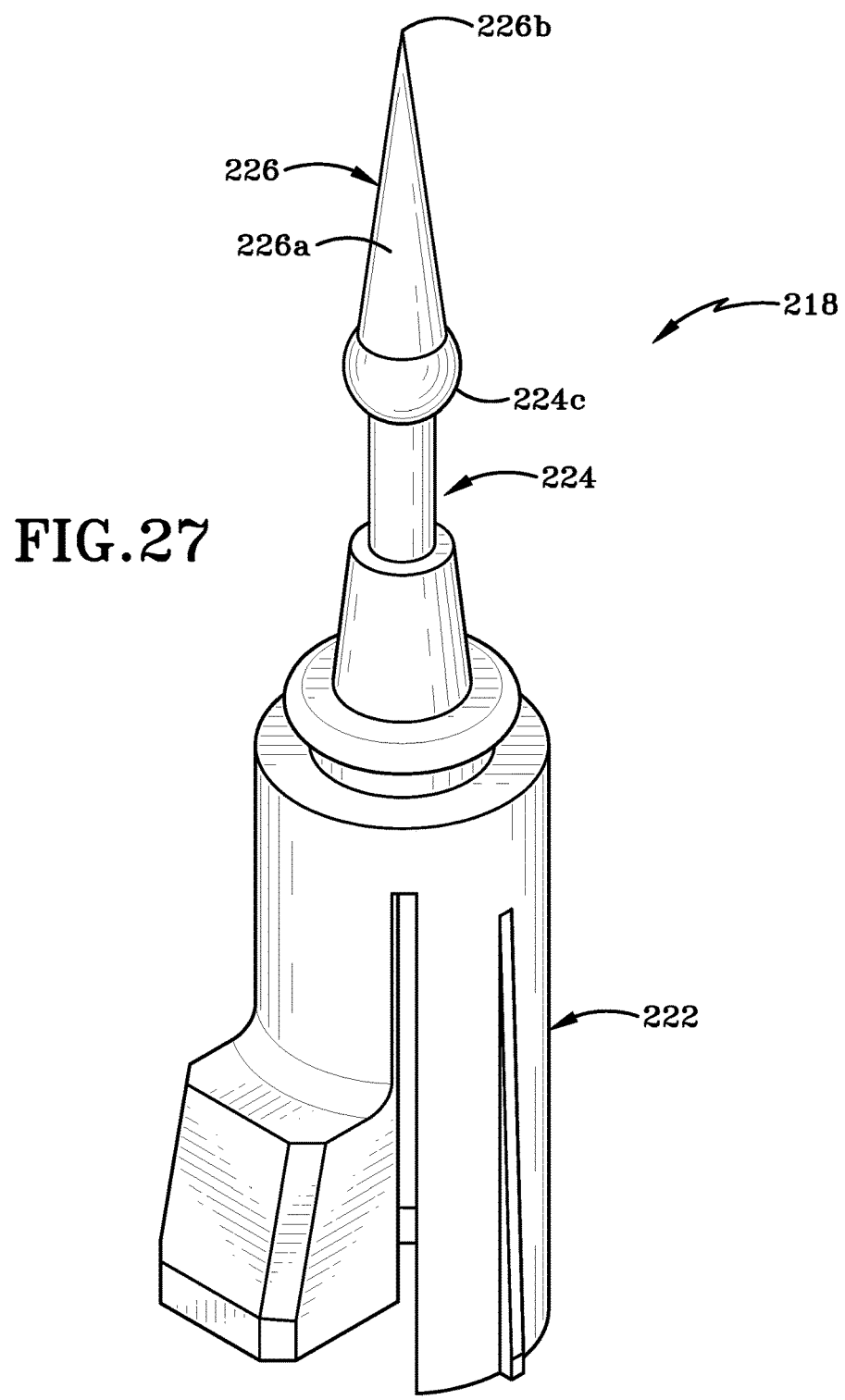

DENTAL IMPLEMENT AND METHOD OF USING THE SAME

CROSS-REFERENCE TO RELATED APPLICATIONS

This application claims the benefit of U.S. Provisional Patent Application Ser. No. 62/170,229 filed Jun. 3, 2015, the entire disclosure of which is incorporated herein by reference.

BACKGROUND

Technical Field

This invention relates generally to dental implements. More particularly, the invention is directed to devices for interproximal cleaning. Specifically, this invention relates to a dental implement including a housing assembly and a removable cap; where the assembly includes a sleeve having a plurality of discrete, individual cartridges therein; each cartridge having a cleaning tip such as an interproximal brush, and wherein the cartridges are progressively movable through the sleeve's bore until one of the cartridges locks into position at a first end of the sleeve and such that the cleaning tip thereof extends outwardly from the first end of the sleeve and is usable to clean between adjacent teeth in a user's mouth.

BACKGROUND INFORMATION

One of the most important parts of the body that people need to take care of properly is their teeth. Studies are showing that dental health contributes to a person's overall health and failure to maintain adequate oral hygiene may place a person at risk for a variety of health issues.

An aspect of oral hygiene that has gained attention over the past decades is the need for removal of food particles that tend to accumulate between the teeth and under the gum line. Since the invention of the first flossing thread in 1815, to the first toothpick in 1869, to present day interproximal brushes, inventors have been relentless in the pursuit of developing self-care products that may perform this vital job of cleaning between the teeth.

Many studies show that flossing thread, the most commonly used interproximal product, is difficult for the average person to use properly and is therefore less effective in the prevention of plaque build up, gingivitis, and periodontitis. Using a simple wooden or plastic toothpick removes some food debris but may not do an effective cleaning job in and of itself. Additionally, manual toothbrushes are unable to adequately penetrate and clean the interproximal space. This space is considered by many to be the cradle of a number of oral diseases, staining of the teeth, and of bad breath.

SUMMARY

There is therefore a continued need in the art for an improved dental implement that more fully addresses the deficiencies of previously known devices and which can aid a person in maintaining proper oral hygiene.

A dental implement for cleaning interproximal spaces and a method of using the same is disclosed herein and this dental implement solves many of the problems found with previously known devices. The dental implement disclosed herein includes a housing assembly having a sleeve with a wall with first and second ends. A bore is defined in the sleeve and this bore extends between the first and second ends thereof. At least one cartridge may be insertable into the bore of the sleeve and be selectively movable therealong. The at least one cartridge may be lockable in the bore. The cartridge includes a cleaning tip extending outwardly from one end. The cartridge is progressively moved along the bore of the sleeve until the cleaning tip extends outwardly from the first end of the sleeve and the cartridge locks into a cleaning position. The cleaning tip may include an interproximal brush. A cap is selectively placeable over the cleaning tip and first end of the sleeve. The cap is provided to protect the tip and keep the tip in a hygienic environment and ready for use.

In one aspect, the invention may provide a dental implement comprising a sleeve having a wall with a first end and a second end; said sleeve defining a bore that extends between the first and second ends; and a first cartridge provided with a first cleaning tip; wherein the first cartridge is received within the bore and is movable therealong; said first cartridge being selectively positioned within the bore such that the first cleaning tip extends outwardly beyond the first end of the sleeve. In another aspect, the dental implement may include a cap that is selectively engageable with the first end of the sleeve to cover the first cleaning tip.

In another aspect, the invention may provide a method of cleaning an interproximal space in a person's mouth; said method comprising providing a dental implement having a sleeve having a wall with a first end, a second end, and a bore defined between the first and second ends; and a first cartridge movable along the sleeve's bore of the sleeve; wherein the first cartridge includes a first cleaning tip; selectively moving the first cartridge along the bore to a position proximate the first end of the sleeve; extending the first cleaning tip on the first cartridge outwardly beyond the first end of the sleeve; and using the first cleaning tip in a person's mouth.

In yet another aspect, the method may provide holding the sleeve and inserting the first cleaning tip into the interproximal space between adjacent teeth in the person's mouth; and moving the first cleaning tip back-and-forth, up-and-down; and from side-to-side between the teeth and removing particulate material from the teeth and from the interproximal space.

In another aspect the invention may provide a teeth cleaning assembly comprising a plurality of cartridges, each cartridge having a base with a first end and a second end; a cleaning tip extending outwardly from the first end and a bore defined in the base, where the bore is accessible through an opening in the second end of the base; wherein the plurality of cartridges are stacked one on top of the other such that the cleaning tip of a first one of the cartridges is received within the cavity of an adjacent second one of the cartridges; and wherein adjacent cartridges in the stack of cartridges are interlockingly engaged with each other; and wherein an uppermost one of the stack of cartridges is detachable from the stack after use of the cleaning tip thereon.

BRIEF DESCRIPTION OF THE SEVERAL VIEWS OF THE DRAWINGS

A sample embodiment is set forth in the following description, is shown in the drawings and is particularly and distinctly pointed out and set forth in the appended claims.

FIG. 3 is a left side elevation of the dental implement's housing assembly;

FIG. 4 is a front elevation of the dental implement's housing assembly;

FIG. 5 is an exploded isometric perspective view of the housing assembly showing a sleeve, a plurality of cartridges and a bottom cover;

FIG. 9 is a top plan view of the single cartridge;

FIG. 10 is a longitudinal cross-section of the single cartridge taken along line 10-10 of FIG. 9;

FIG. 27 is an isometric perspective view of a third embodiment of a single cartridge from use in the housing assembly.

Similar numbers refer to similar parts throughout the drawings.

DETAILED DESCRIPTION

Figure 1:
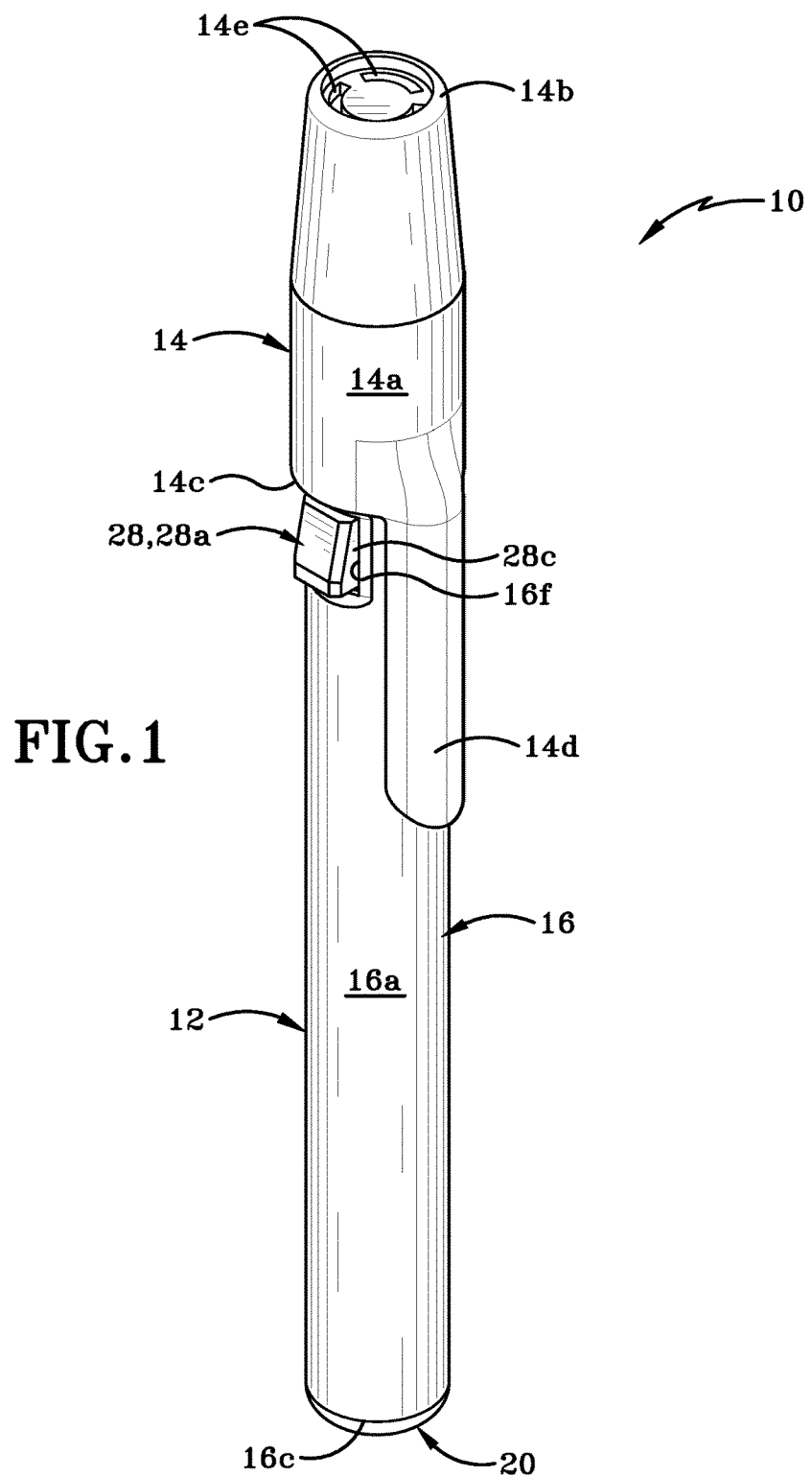
FIG. 1 is an isometric perspective view of a top end, front, and right side of a dental implement in accordance with an aspect of the invention showing a housing assembly with a cap engaged therewith.
Figure 2:
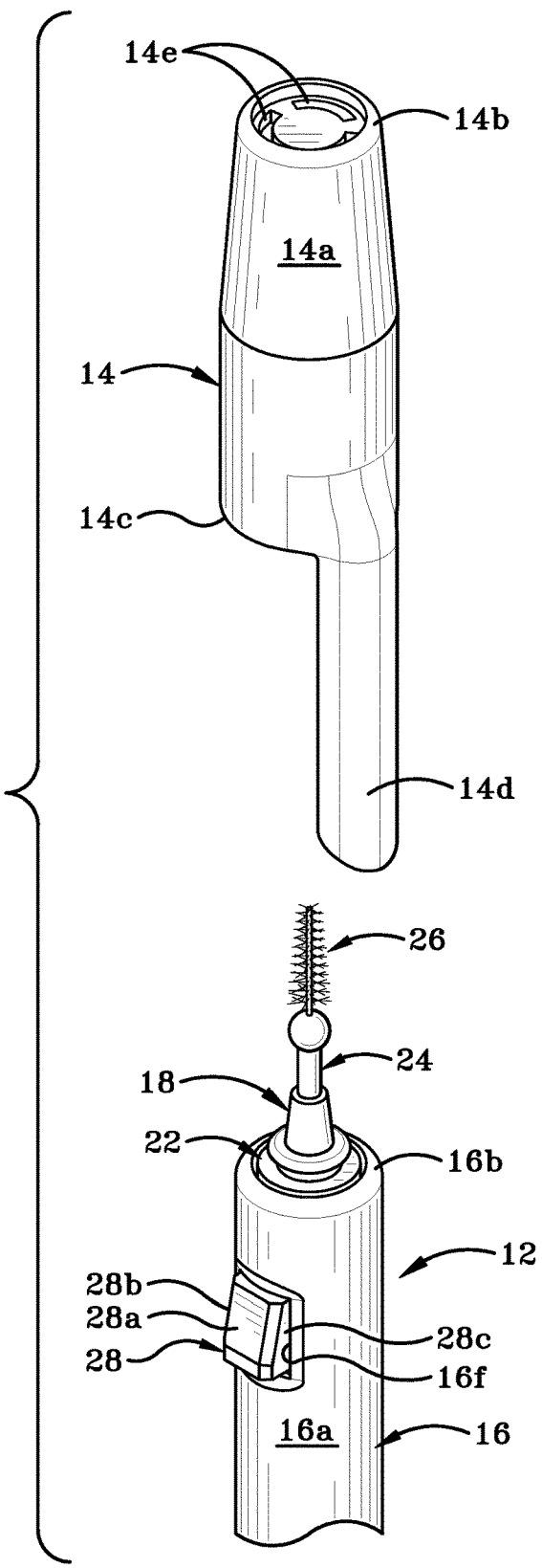
FIG. 2 is an exploded isometric perspective view of a first end of the housing assembly with the cap disengaged therefrom.
Figure 6:
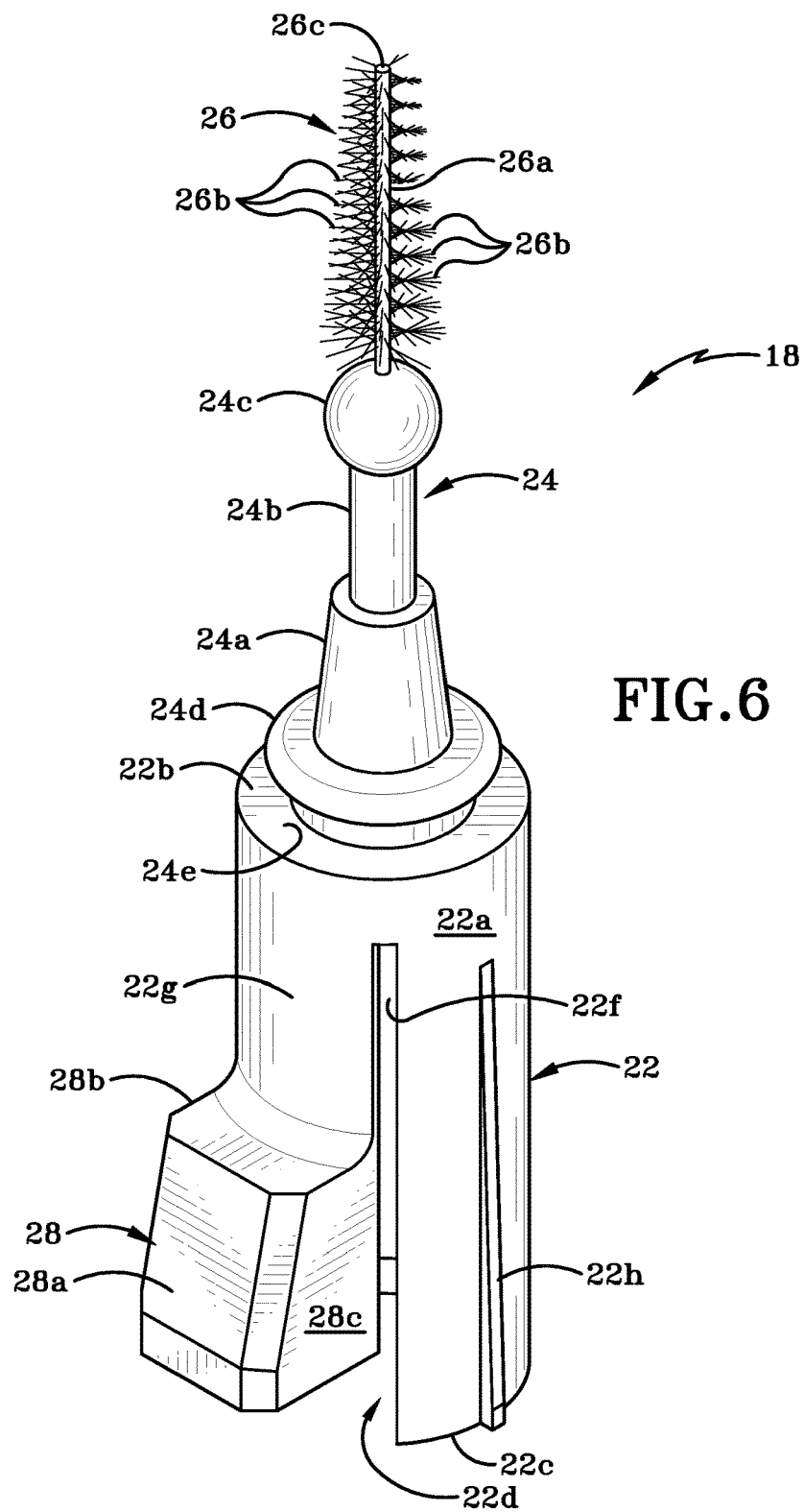
FIG. 6 is an enlarged isometric perspective view of a single cartridge showing the top, the front and ridge side thereof.
Figure 7:
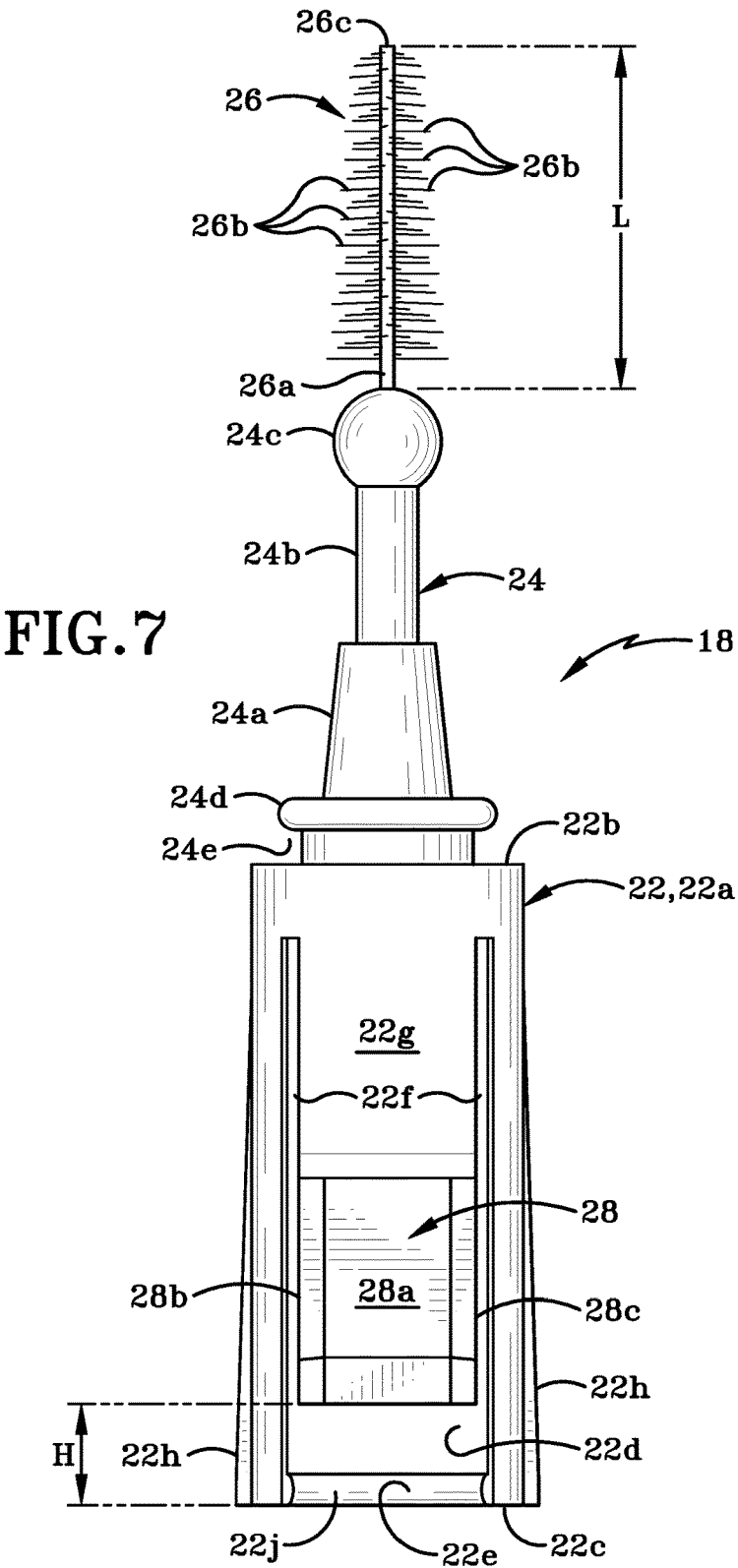
FIG. 7 is an enlarged front view of the single cartridge.

Referring to FIGS. 1-25, the dental implement of the present invention is generally indicated at 10. Dental implement 10 is comprised of a housing assembly 12 and a cap 14. As illustrated in FIGS. 1 and 2, dental implement 10 may be shaped and sized to have an appearance similar to a pen. Cap 14 is configured so that it may be used to clip dental implement 10 to any suitable article, such as to a shirt pocket, for instance.

Housing assembly 12 comprises a sleeve 16 (FIG. 5) and one or more cartridges 18 that are loadable into sleeve 16. Sleeve 16 may be fabricated so that the sleeve may be used multiple times. Cartridges 18 may be fabricated so that they are disposable after a single use or after a relatively short period of use. Alternatively, sleeve 16 and cartridges may be disposable after a single use or a short period of use. Sleeve 16 and cartridges 18 will be described in greater detail hereafter.

Figure 13:
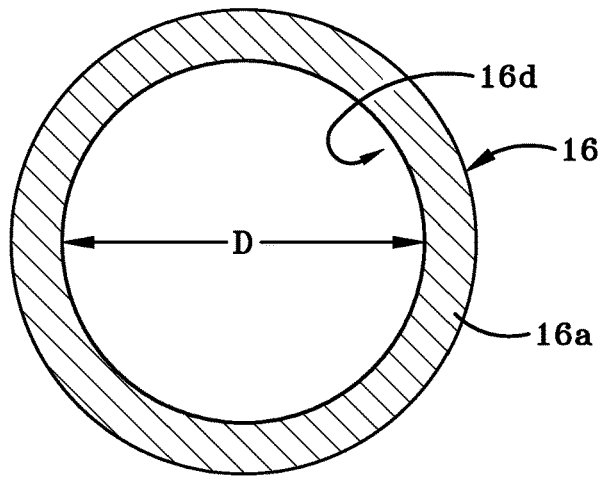
FIG. 13 is a cross-section of the sleeve taken along line 13-13 of FIG. 11.

Referring to FIGS. 11-15, sleeve 16 comprises a tubular member that may be generally circular in cross-section (see FIG. 13). Sleeve 16 includes a generally cylindrical exterior wall 16a, a first wall at a first end 16b of wall 16a, and a second wall at a second end 16c of wall 16a. Sleeve 16 has a longitudinal axis "Y" that intersects first end 16b and second end 16c and extends along the length of sleeve 16; where the length is measured from first end 16b to second end 16c. First and second ends 16b, 16c may be oriented at right angles to longitudinal axis "Y". A bore 16d (FIG. 12) bounded and defined by wall 16a and bore 16d extends from first end 16b to second end 16c. Bore 16d is therefore orientated parallel to longitudinal axis "Y". Bore 16d is accessible through a first opening 16b' (FIGS. 5 and 12) defined in first end 16b and through a second opening 16c defined in second end 16c.

Figure 14:
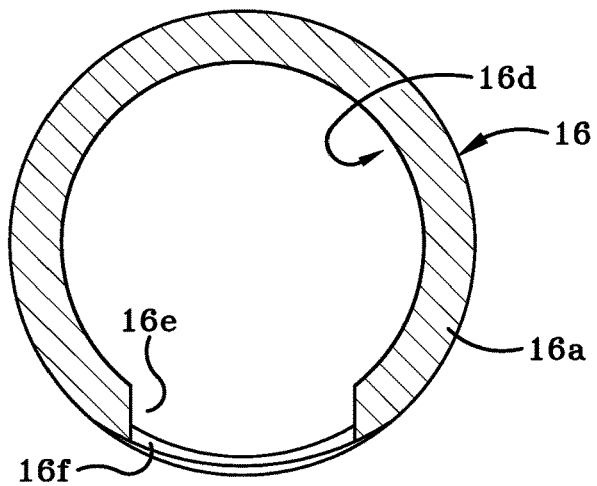
FIG. 14 is a cross-section of the sleeve taken along line 14-14 of FIG. 11.
Figure 15:
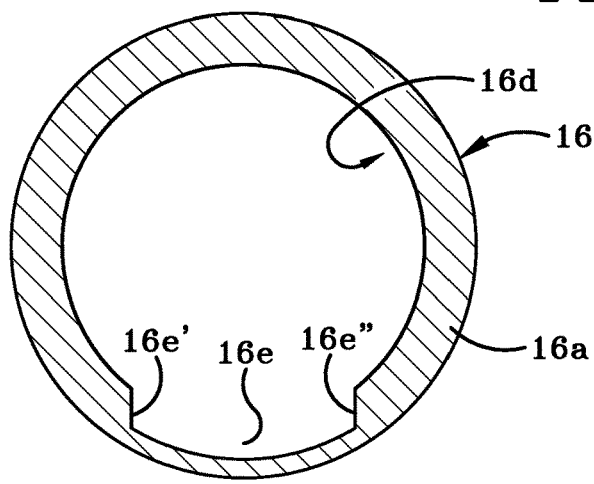
FIG. 15 is a cross-section of the sleeve taken along line 15-15 of FIG. 11.

As is best seen in FIGS. 14 and 15, a channel 16e is defined in an interior surface of wall 16a. Channel 16e may originate proximate second end 16c and extend to proximate first end 16b. Alternatively, channel 16e may terminate a distance inwardly from first end 16b. Channel 16e may be oriented substantially parallel to longitudinal axis "Y" and is substantially continuous with bore 16d.

An aperture 16f is defined in wall 16a of sleeve 16. Aperture 16f is located a distance inwardly from first end 16*b* of sleeve 16. Aperture 16*f* is in fluid communication with bore 16*d*. Furthermore, aperture 16*f* opens into and is aligned with channel 16*e*.

Figure 17:
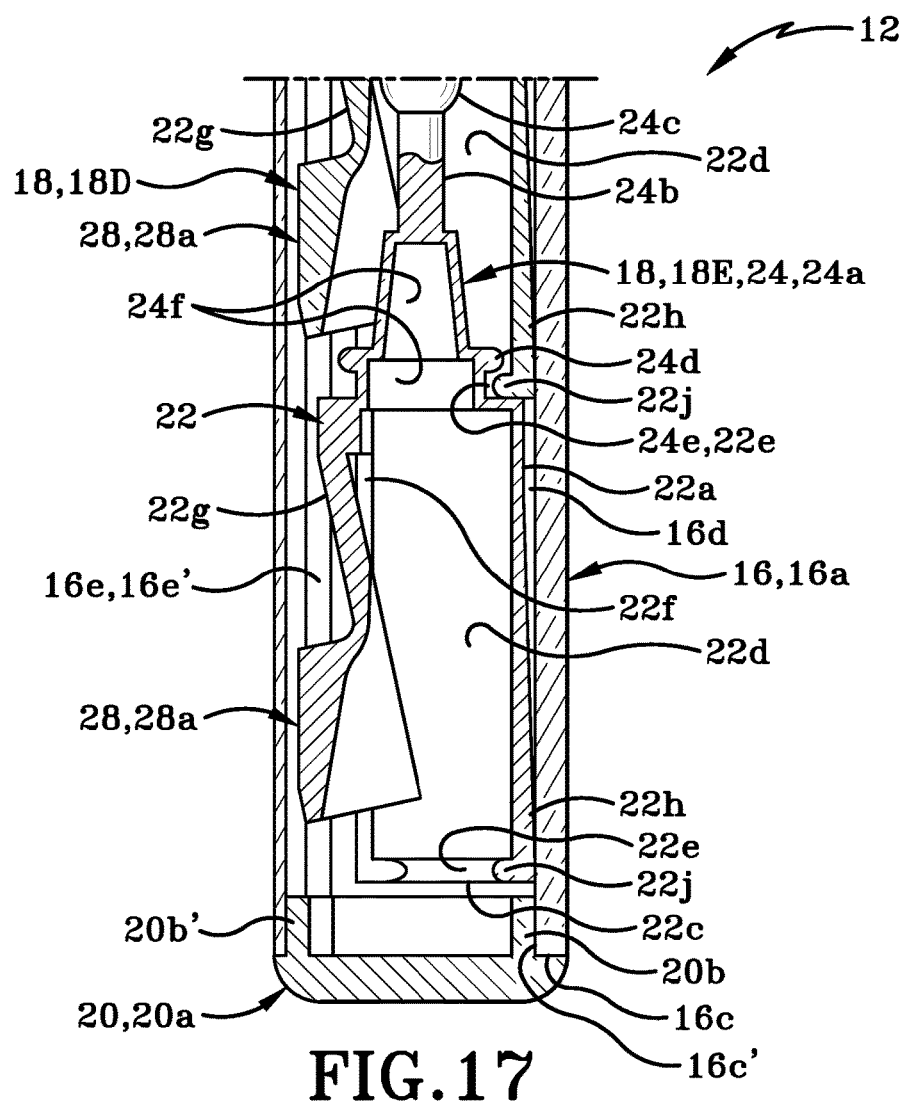
FIG. 17 is a longitudinal cross-section of a second region of the housing assembly taken along line 17-17 of FIG. 4.

A cover 20 may be provided to selectively close off access to bore 16*d*. Cover 20 is shaped to be engaged with second end 16*c* of sleeve 16 and to thereby close off access to bore 16*d* through second opening 16*c'*. Cover 20 may be selectively removed to gain access to bore 16*d* through second opening 16*c'*. Cover 20 includes a base region 20*a* and a detent region 20*b* that extends outwardly from base region 20*a*. Detent region 20*b* is shaped and sized to be substantially complementary to bore 16*d* and includes a region 20*b'* that is configured to be received in channel 16*e*. Detent region 20*b* is received within bore and channel 16*d*, 16*e* and base region 20*a* is located outside of bore 16*d* and forms the end of the housing assembly 12. The engagement of cover 20 with sleeve is illustrated in FIG. 17.

Wall 16*a* of sleeve 16 may be fabricated from a transparent plastic material so that any cartridges 18 located within bore 16*d* may be visible or at least partially visible from outside the sleeve 16. The material used to fabricate sleeve 16 may be colored in addition to being transparent so as to be more aesthetically pleasing to the consumer. Cap 14 may be similarly fabricated from a colored and/or transparent plastic material. Sleeve 16 and cap 14 may be colored in a similar fashion or the two components may be differently colored to provide a different aesthetic. Any decorative or instructive markings may be applied to the exterior surface of wall 16*a*. For example, the exterior surface of wall 16*a* may include instructions, either pictorial or textual, to show how to use dental implement 10 or how to move cartridges 18 through sleeve 16 (as will be described later herein). Alternatively, dental implement 10 may be sold in packaging that may include instructions as to how to use dental implement, reload a series of cartridges therein or any other information useful to the consumer about the product or its use. In other instances, the exterior surface of wall 16*a* may include patterns or images to make sleeve 16 visually appealing.

As indicated previously, housing assembly 12 includes one or more cartridges 18. Each individual cartridge 18 is able to be used as a dental hygiene tool. Cartridges 18 may be configured to be used in one of a plurality of different dental hygiene procedures. For example, FIGS. 1-25 illustrate a first style of cartridge 18; FIG. 26 illustrates a second style of cartridge 118, and FIG. 27 illustrates a third style of cartridge 218. Each of the cartridges 18, 118 and 218 may be used for a different dental hygiene procedure. By way of example, cartridge 18 may be used as an interdental flosser; cartridge 118 may be used as a toothpick and cartridge 218 may be utilized as a gum massager or stimulator. It will be understood that cartridges that are useful for other dental hygiene procedures from those described herein may be utilized as part of housing assembly 12. Such different cartridges could include those having components that may be useful for descaling, polishing or even application of whiteners.

Cartridge 18 will be described in greater detail, reference being made to FIGS. 6-10. Cartridge 18 comprises a base 22, a mounting member 24, and a cleaning tip 26. Cartridge 18 or parts thereof may be blow molded, injection molded or formed in any other manner. Base 22 and mounting member 24 may be formed as an integral, unitary or monolithic component. In other instances, base 22 and mounting member 24 may be separately molded or otherwise fabricated and are then engaged to each other by any suitable means such as by heat welding or an adhesive. (If the latter, adhesives that are safe for human consumption are contemplated as being suitable for cartridge 18). Alternatively, cleaning tip 26 may be integrally formed with both base 22 and mounting member 24 to form a unitary or monolithic component. Still further, cleaning tip 26 may be integrally formed with mounting member 24 to form a unitary or monolithic component that is then engaged with base 22 by any suitable means.

Base 22 may include a peripheral wall 22*a*, a first wall at a first end 22*b* of peripheral wall 22*a*, and a second wall at a second end 22*c* of wall 22*a*. Wall 22*a* is configured to be complementary in shape to at least a portion of bore 16*d* of sleeve 16. If bore 16*d* is other than generally circular in cross-sectional shape then wall 22*a* will be formed to be other than generally circular in cross-sectional shape. As illustrated in FIG. 13, wall 22*a* of base 22 may comprise a generally cylindrical component that has a diameter that is only slightly smaller than a diameter "D" of bore 16*d*.

Wall 22*a* bounds and defines a chamber 22*d* that extends from first end 22*b* to second end 22*c* thereof. An opening 22*e* (FIG. 10) is defined in second end 22*c* and provides access to chamber 22*d*. A pair of longitudinal slots 22*f* may be defined in base 22. Each slot 22*f* originates in second end 22*c* and extends generally parallel to a longitudinal axis "Y1" (FIG. 10) of base 22.

Cartridge 18 is provided with a locking member that selectively fixedly secures the cartridge 18 within bore 16*d* of sleeve 16. The locking member may take any one of a variety of different forms. As illustrated herein, one suitable locking member is provided on base 22 in the form of an arm 22*g* that is defined between the slots 22*f* of base 22. A lower free end of arm 22*g* is enlarged and projects outwardly away from peripheral wall 22*a*. The lower end of arm 22*g* is identified herein by the reference number 28 and comprises what shall be referred to herein as a button 28. Slots 22*f* define between them a larger opening within which arm 22*g* (and button 28) is located. Arm 22*g* is "hinged" to base 22 by a living hinge and is moveable within this larger opening between a first and second position, as will be described hereafter.

Figure 18:
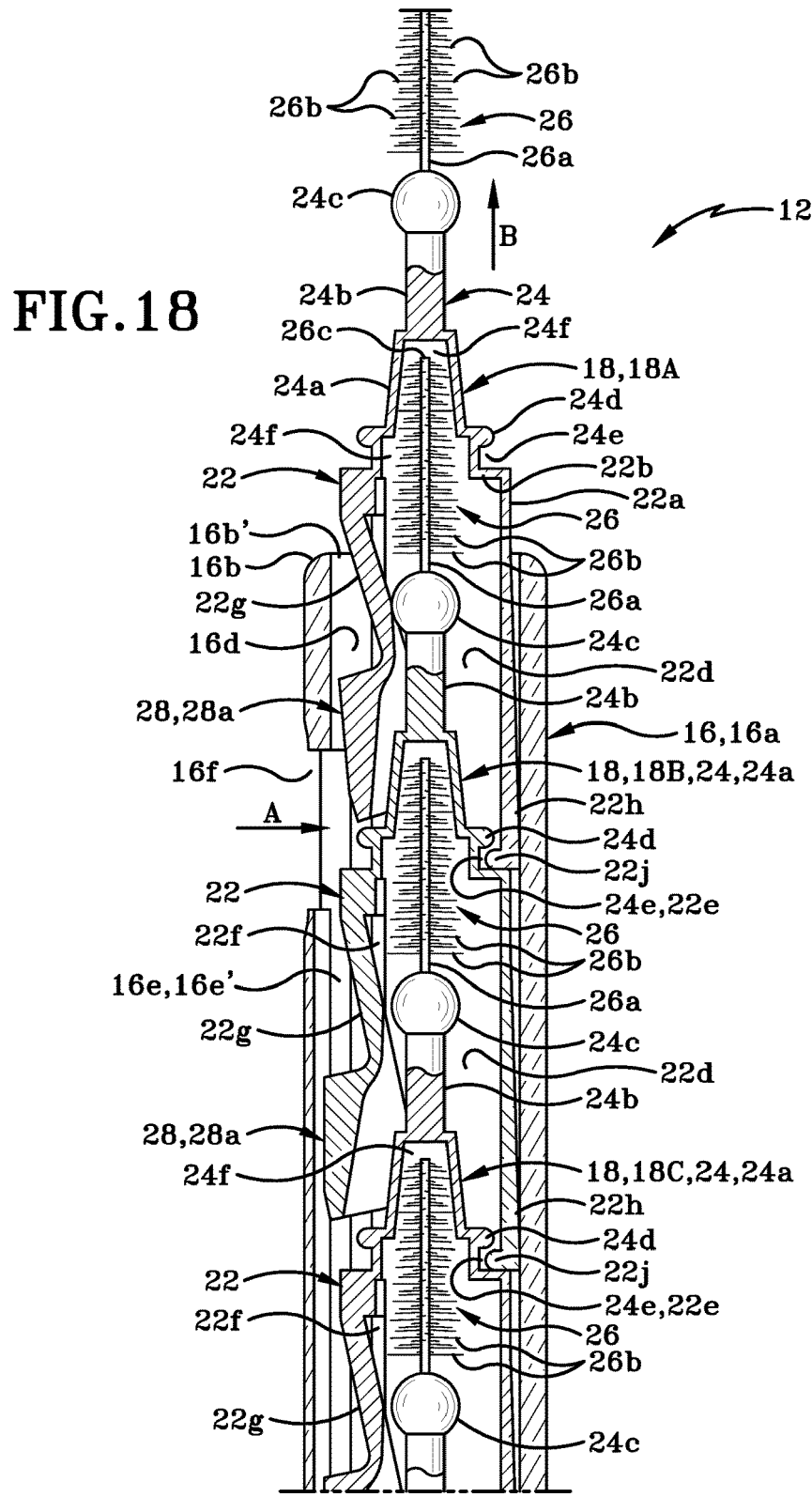
FIG. 18 is a longitudinal cross-section of the first region of the housing assembly showing a first method of removing the first cartridge, said figure illustrating the first cartridge with the button depressed inwardly and the first cartridge being removed from the sleeve of the housing assembly and pulling the rest of the stack of cartridges upwardly through the sleeve's bore.
Figure 19:
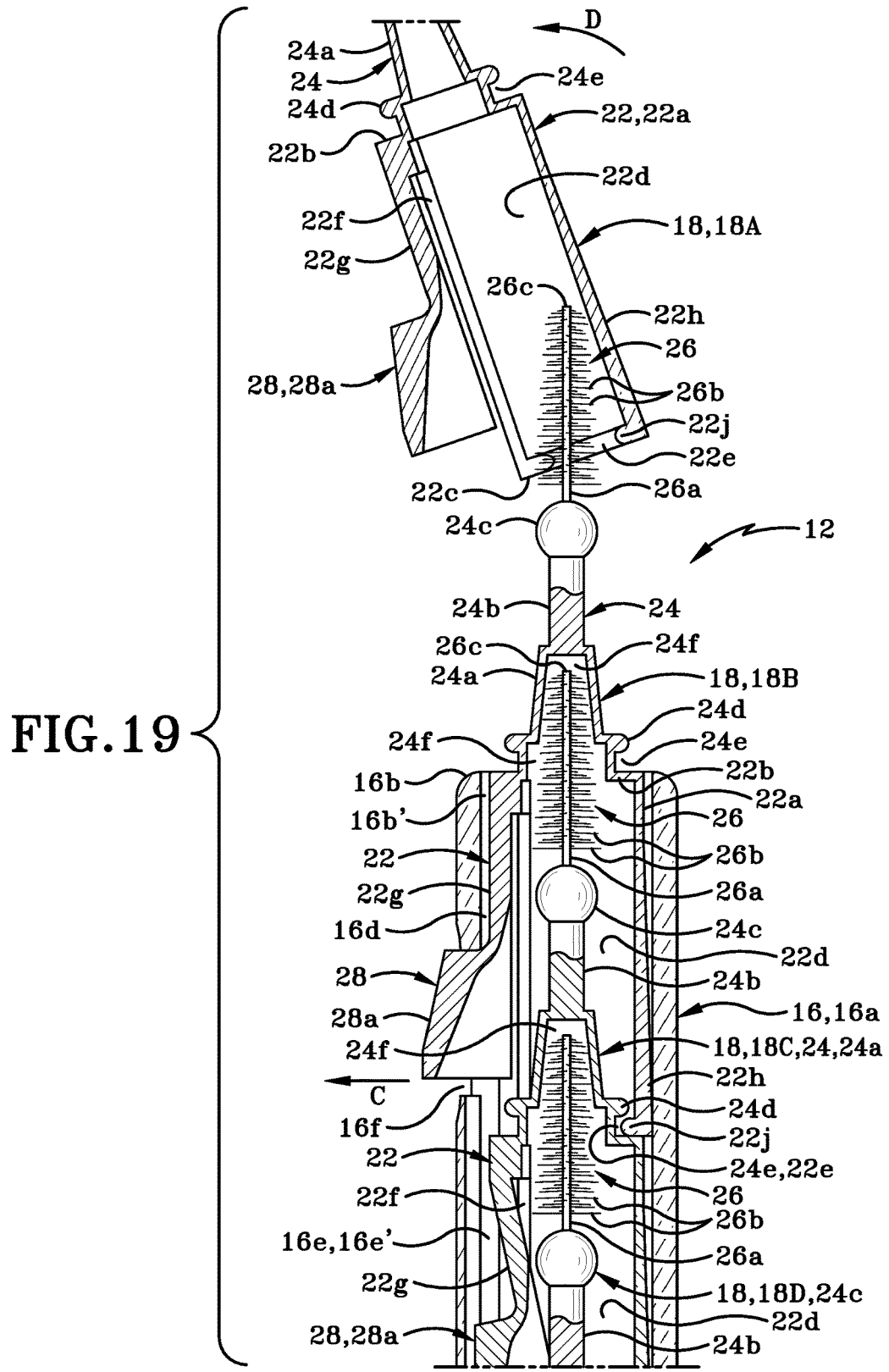
FIG. 19 is a longitudinal cross-section of the first region of the housing assembly as shown in FIG. 18 showing the first cartridge disengaged from the second cartridge and removed from the sleeve and showing the second cartridge in a position ready for use.

As shown in FIGS. 18 and 19, when cartridge 18 is received in bore 16*d* and is moved therealong until button 28 aligns with aperture 16*f*, button 28 moves through aperture 16*f* and secures cartridge 18 in a fixed position within the bore 16*d*. Arm 22*g* is effectively a spring-loaded locking member that is movable between a first position and a second position. Button 28 and part of arm 22*g* are depressible inwardly into the chamber 22*d* of base 22 when a force is applied to button 28. In this first position (i.e., button 28 and arm 22*g* depressed inwardly) cartridge 18 is able to move along bore 16*d* of sleeve. When that force is released, arm 22*g* and therefore button 28 will return to their original position, i.e., the second position. If button 28 is aligned with aperture 16*f* then the button 28 will move to the second position and then movement through bore 16*d* will be prevented and cartridge 18 will be locked in a fixed position within bore 16*d*. Aperture 16*f* is located a distance downwardly from first end 16*b* of sleeve 16. Cartridge 18 is sized so that when button 28 interlocks with aperture 16*f*, cleaning tip 26 will extend outwardly beyond first end 16*b* of sleeve 16.

Figure 8:
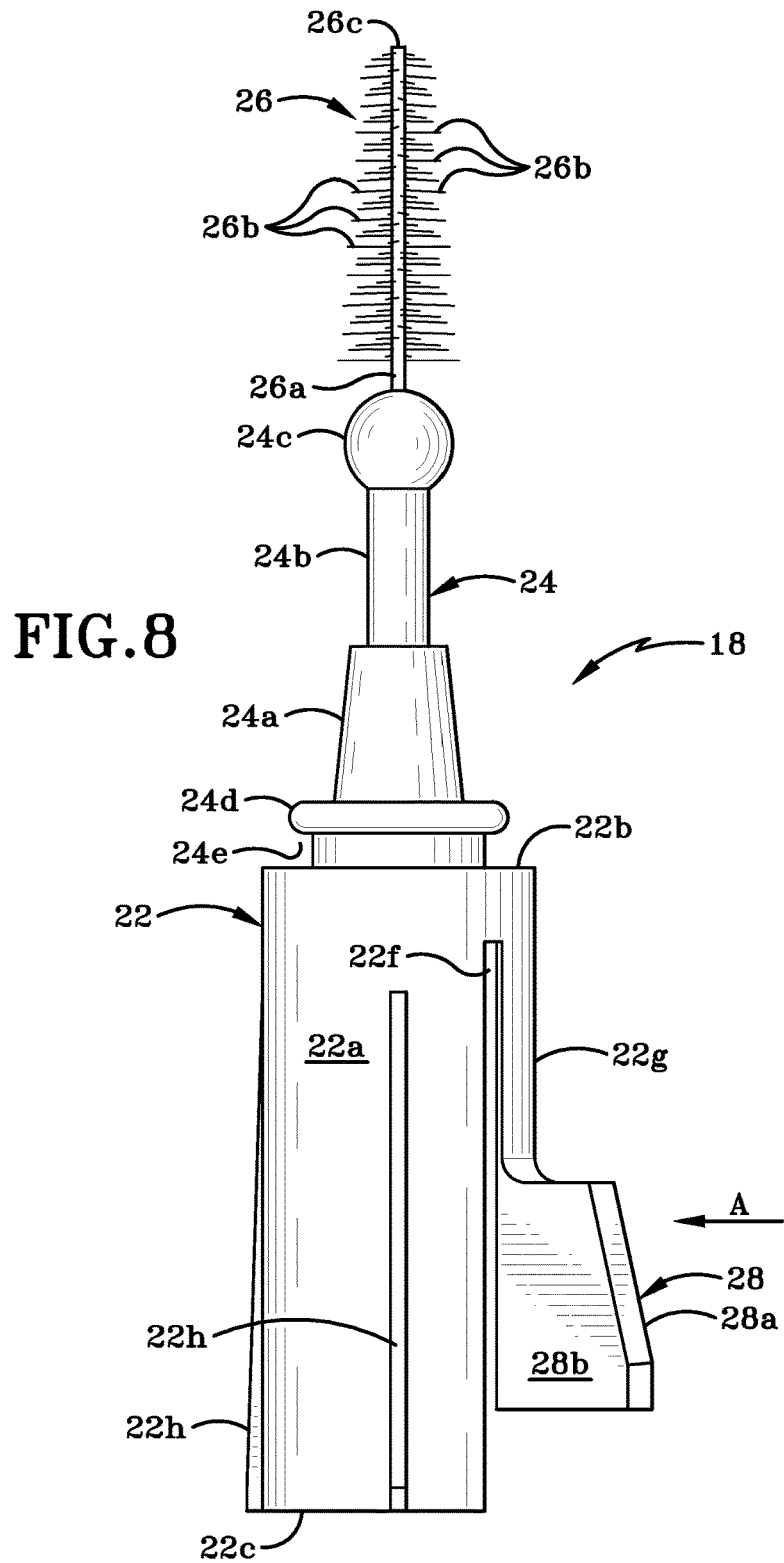
FIG. 8 is an enlarged left side elevation of the single cartridge.
Figure 11:
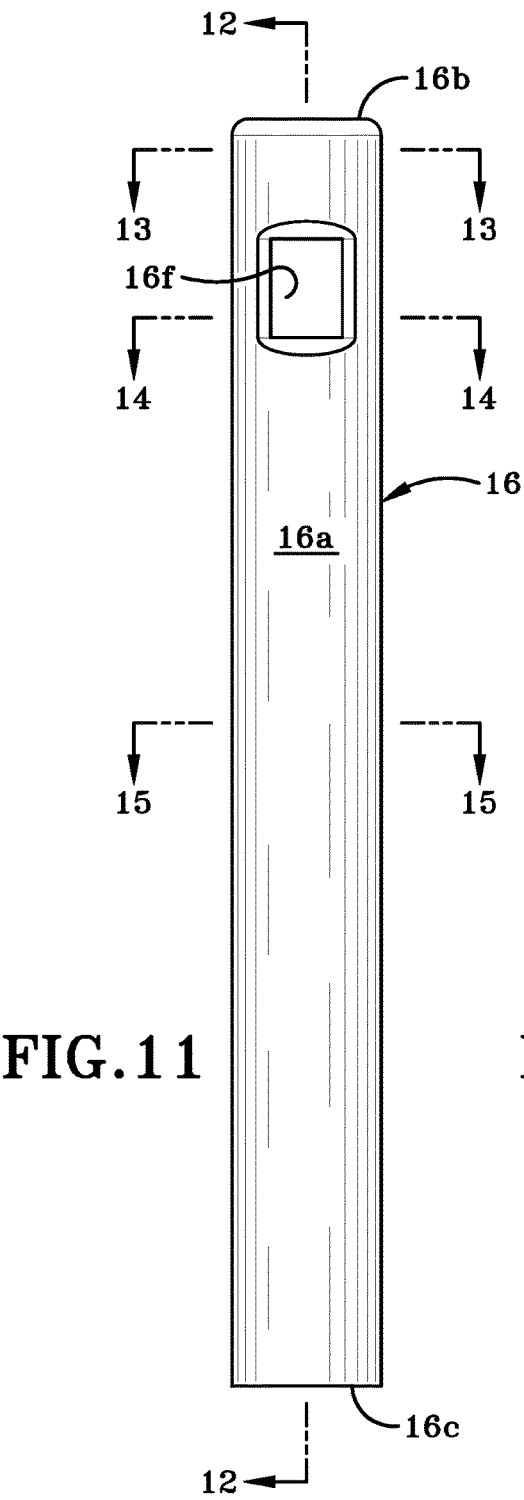
FIG. 11 is a front elevation of the sleeve of the housing assembly shown on its own.
Figure 12:
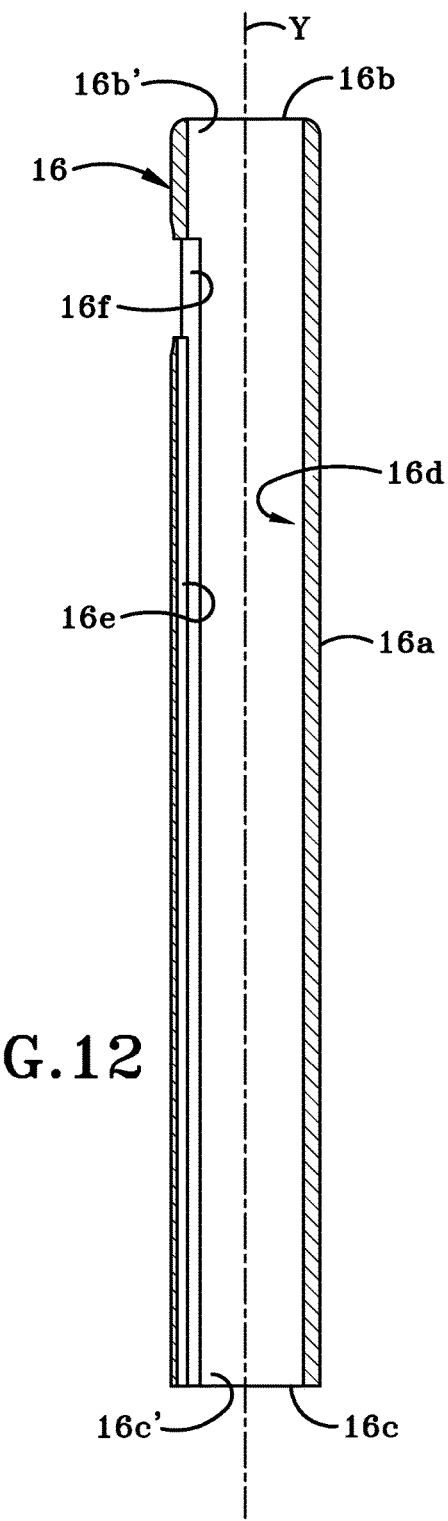
FIG. 12 is a longitudinal cross-section of the sleeve taken along line 12-12 of FIG. 11.

Button 28 includes an angled face 28*a* (FIG. 6) that is positioned so as to be contacted by a user's finger when dental implement 10 is to be used (as will be later described herein). Since arm 22*g* is separated from peripheral wall 22*a* by slots 22*f*, arm 22*g* is able to be depressed inwardly for a distance into chamber 22*d* by pushing on button 28 in the direction of arrow "A" (FIG. 8). When face 28a is pushed inwardly toward the interior surface of base 22 opposite arm 22g, in the direction of arrow "A", substantially the entire arm 22g is able to flex inwardly toward the interior surface opposite arm 22g. When the force on face 28a is released, the spring force in arm 22g causes arm 22g to move outwardly away from the interior surface of the wall 16a in the direction indicated by arrow "C" and arm 22g returns to its original position. As indicated in FIGS. 18 and 19, the movements indicated by arrow "A" and arrow "C" are movements that are substantially at right angles to longitudinal axis "Y1". Arrow "B" indicates movement in a direction that is substantially parallel to longitudinal axis "Y".

As is best seen from FIG. 10, button 28 does not extend all the way downwardly to second end 22c of peripheral wall 22a. Instead, a lowermost region of button 28 is located a distance "H" (FIG. 10) inwardly from second end 22c. The fact that arm 22g is shorter than peripheral wall 22a makes it possible for button 28 to be depressed inwardly into chamber 22d and to return to its original non-depressed position without interference.

Base 22 also includes one or more ribs 22h that extend outwardly from an exterior surface of peripheral wall 22a for a distance. The extent to which the ribs 22h extend outwardly from the exterior surface is greater proximate second end 22c than is the case proximate first end 22b. Thus, ribs 22h flare outwardly away from the exterior surface of peripheral wall 22a in a direction moving from first end 22b towards second end 22c. Ribs 22h are provided to engage the interior surface of wall 16a of sleeve 16 when cartridge 18 is received within bore 16d. Ribs 22h keep cartridge 18 correctly oriented within bore 16d and minimize the frictional contact between wall 16a and wall 22a so that cartridge 18 may move within bore 16d, as will be later described herein. Ribs 22h may also serve to strengthen base 22 and aid in ensuring that arm 22g is able to flex relative to the rest of base 22 instead of the wall 22a collapsing when force is applied to button 28. Ribs 22h may be oriented generally parallel to longitudinal axis "Y1". An annular protrusion 22j bounds and defines at least a part of the opening 22e and is located adjacent second end 22c.

Mounting member 24 extends upwardly and outwardly from first end 22b of base 22. Mounting member 24 may include a frustoconical first region 24a, a shaft 24b extending outwardly from first region 24a, and a bulbous second region 24c. Frustoconical first region 24a includes an annular ring 24d that is located a distance outwardly from first end 22b of base 22 and extends a distance outwardly from an exterior surface of first region 24a. A gap 24e (FIG. 8) is defined between ring 24d and first end 22b. FIG. 10 also shows that a chamber 24f is bounded and defined by first region 24a of mounting member 24. Chamber 24f is in fluid communication with cavity 22d and forms an uppermost region of cavity 22.

Figure 16:
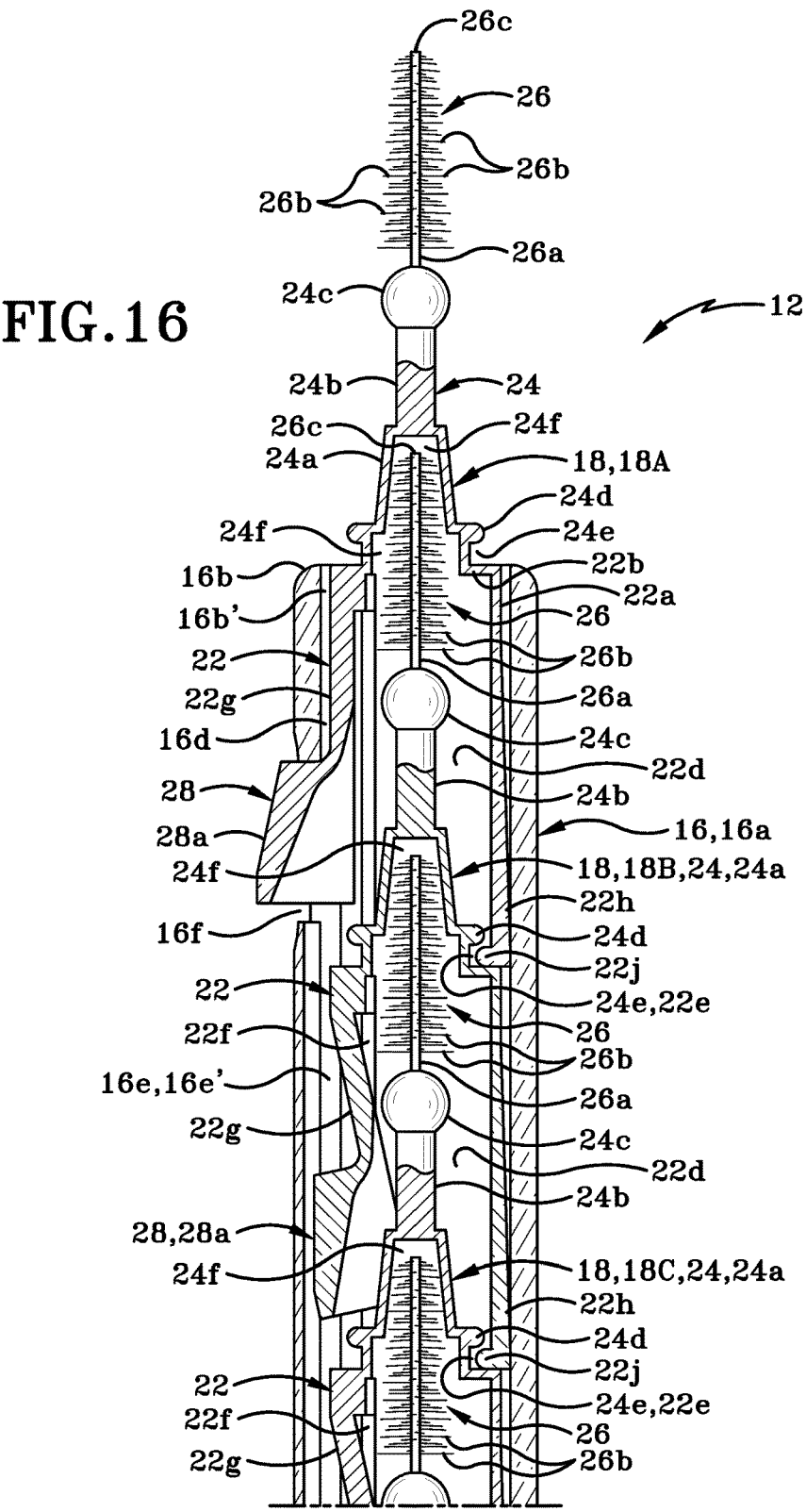
FIG. 16 is a longitudinal cross-section of a first region of the housing assembly taken along line 16-16 of FIG. 4.

First region 24a may be of a diameter that is smaller than the exterior diameter of base 22 (which approximates the diameter "D" of bore 16d of sleeve 16). Ring 24d extends outwardly for a distance from first region 24a such that the diameter of mounting member 24 at ring 24d is greater than the rest of first region 24a. Shaft 24b may be smaller in diameter than the minimum diameter of first region 24a proximate shaft 24b. Second region 24c may be of a diameter similar to the minimum diameter of first region 24a and is therefore larger than the diameter of shaft 24b. The reduced relative diameter of shaft 24b makes it possible for shaft 24b to flex relative to first region 24a. Furthermore, first region 24a, shaft 24b, second region 24c and ring 24d are all of a diameter smaller than a diameter of opening 22e in base 22. This configuration makes it possible for first region 24a (including ring 24d), shaft 24b and second region 24c of one cartridge 18 to be received through the opening 22e in base 22 of a cartridge located about it in order for two or more cartridges 18 to be arranged in a stack one on top of the other. This is illustrated in FIGS. 5 and 16-21. Cartridges 18 are thus configured to be stackable one on top of the other and are shaped and sized to nest with each other. When two or more cartridges 18 are arranged in such a stack annular protrusion 22j that bounds and defines opening 22e of the upper cartridge 18A (FIG. 16) is received in the gap 24e defined between ring 24d and first end 22b of the lower cartridge 18B (FIG. 16). This arrangement interlocks the upper and lower cartridges 18A, 18B together and causes the cartridges to be able to move in unison with each other. FIG. 5 shows five cartridges stacked one on top of the other and interlocked with each other as described above. The first cartridges are identified as cartridges 18A, 18B, 18C, 18D, and 18E. Still further, when cartridges (such as cartridge 18A and 18B are stacked one on top of the other, cleaning tip 26 on the lower cartridge 18B may extend from chamber 22d defined in base 22 and into chamber 24f defined by mounting member 24 of upper cartridge 18A.

It will be understood that while five cartridges 18A-18E are illustrated herein as being stacked one on top of the other, it will be understood that dental implement 10 may include only a single cartridge 18 or two or more cartridges and may include more than the five cartridges illustrated herein. In other words, any desired number of cartridges 18 may be engaged in a sleeve 16 to form a housing assembly 10.

In accordance with another aspect of the invention, cleaning tip 26 extends outwardly from the bulbous second region 24c of mounting member 24. Cleaning tip 26 may take any one of a number of different configuration such as is the one shown in FIGS. 2-21. In this particular instance, cleaning tip 26 comprises an interproximal or interdental brush, i.e., a bristled brush that is designed to be inserted into the space or gap between adjacent teeth. Cleaning tip 26 may be in the form of a brush and comprise a wire member 26a and a plurality of bristles 26b. One end of wire member 26a may be embedded, integrally formed or otherwise secured in second region 24c. Wire member 26a extends outwardly from second region 24c in a direction generally parallel to longitudinal axis "Y1". Bristles 26b may be engaged wire member 26a and extend outwardly therefrom. Alternatively, bristles 26b may be integrally formed with wire member 26a and extend outwardly therefrom. It will be understood that wire member 26a may be comprised of a different material to bristles 26b or may be comprised of the same material as bristles 26b. The term "wire" should not be narrowly interpreted as indicating that the member 26a is made from metal. Wire member 26a may be entirely comprised of plastic or any other suitable material and may be formed as intertwined strands or as a single unitary component of substantially constant diameter. Bristles 26b may be oriented substantially at right angles to longitudinal axis "Y1" or may be oriented at another angle relative thereto. Each bristle 26b may be a single filament or may be tufted and be comprised of several filaments.

In accordance with one aspect of the invention, the bristles 26b adjacent second region 24c may be of a greater length than the bristles 26b remote therefrom. The degree to which bristles 26b may extend outwardly from wire member 26b from proximate second region 24c to proximate a terminal end 26c of cleaning tip 26 thus may gradually decrease. When cartridge 18 is viewed from the side, such as in FIG. 6, the cleaning tip 26 may therefore taper in shape from second region 24c toward terminal end 26c. Wire member 26a and bristles 26b thereon are sized to be suitable for introduction into interproximal spaces in a user's mouth, i.e., into the spaces between adjacent teeth and which are occupied by gum tissue. Additionally, the overall length "L" (FIG. 7) of the cleaning tip 26 on cartridge 18 is long enough to be used to effectively clean these interproximal spaces when moved back and forth.

It should be noted that cleaning tip 26 may be fabricated from a material that gives it flexibility, strength and resilience. Suitable materials for part or all of cleaning tip 26 may include metals or materials made up in part of metals such as titanium. Additionally, and/or alternatively the provision of the thinner shaft 24b on cartridge 18 imparts flexibility to the cleaning tip 26. The flexibility of cleaning tip 26 is such that during use, the tip 26 may flex and bend so that the tip 26 will move easily around and across teeth surfaces and between adjacent teeth. So, when housing assembly 12 is moved back and forth and up and down during a cleaning operation, bristles 26b on cleaning tip 26 may encounter the surfaces to be cleaned at a variety of angles and thereby more effectively clean the same. The flexibility provided by shaft 24b also ensures that cleaning tip 26 may be manipulated into difficult to reach regions of the user's teeth and mouth.

The resilience of the materials used to fabricate cleaning tip 26 may also ensure that when the cleaning operation is completed, the tip 26 may return to its original position and orientation. In other words, during use thereof the tip 26 will not tend to bend and then remain bent. Instead, the tip 26 will tend to bend during use and then return to its original position and orientation relative to first end 22b of base 22. Most prior art devices will bend when in use but will stay bent once the cleaning operation is finished.

During fabrication, one or more cartridges 18, for instance five cartridges 18A-18E (FIGS. 5, 16 and 17), are stacked or nested together as shown in FIG. 5. It should be noted that cartridges 18A-18B are positioned so that all of the locking members i.e., arms 22g and buttons 28, are aligned with each other. These aligned locking members are positioned to be received within channel 16e of sleeve 16. Sleeve 16 is positioned so that a first one 18A of the cartridges 18 is adjacent second opening 16c'. One or both of sleeve 16 and the cartridge stack are moved relative to each other so that the stack of cartridges is received into bore 16d. It should be noted that, in order for the stack of cartridges to be received into bore 16d, the aligned row of buttons 28 must be oriented to be receivable within channel 16e of sleeve 16. Channel 16e serves two purposes. Firstly, channel 16e keeps cartridges 18A-18E engaged and aligned with each other. This is accomplished by those regions of the wall 16a that define side surfaces 16e' and 16e" (FIG. 15) of channel 16e being angled in a manner complementary to side surfaces 28b and 28c (FIGS. 6-9) of button 28; and by channel 16e being of a narrower width proximate the exterior surface of wall 16a than is the case proximate the interior surface of wall 16a. (The width is measured as the distance between side surface 16e' and side surface 16e"). Additionally, channel 16e keeps the row of buttons 28 aligned with aperture 16f in sleeve 16.

First cartridge 18A enters second opening 16c' to bore 16d in second end 16c. The relative movement between sleeve 16 and the stack of cartridges 18 is continued until the second end 16c of sleeve 16 that circumscribes second opening 16c' encounters arm 22g and particularly encounters angled face 28a on button 28. Continued relative movement causes arm 22g to be depressed inwardly in the direction of arrow "A". Consequently, the entire first cartridge 18A slides into bore 16d of sleeve 16.

Since cleaning tip 26 of second cartridge 18B (FIG. 16) is nested inside chamber 22d and chamber 24f of first cartridge 18A, continued relative movement between sleeve 16 and the stack of cartridges continues until second end 16c of sleeve 16 encounters arm 22g of second cartridge 18B. Again, continued relative movement of sleeve 16 and the cartridges 18 causes arm 22g of second cartridge 18B to be depressed inwardly in the direction of arrow "A" and second cartridge 18B slides into bore 16d of sleeve 16. Because the cleaning tip of third cartridge 18C is nested inside chamber 22d and chamber 24f of second cartridge 18B, continued relative movement of sleeve 16 and cartridges 18 in continues until the arm 22g of third cartridge 18C comes into contact with second end 16c, and so on. Thus, the entire stack of cartridges shown in FIG. 5 is progressively fed into bore 16d of sleeve 16. When the arm of first cartridge 18A reaches aperture 16f, the force being applied on arm 22g of first cartridge 18A, by the presence of the interior wall defining bore 16d, is released. Arm 22g returns to its original, non-compressed position will move in the direction indicated by arrow "C", i.e., opposite to the direction indicated by arrow "A". This movement in the direction "C" will cause button 28 to exit bore 16d and to extend outwardly through opening 16f and for a distance beyond the exterior surface of wall 16a. When button 28 of first cartridge 18A is so positioned, relative longitudinal movement (i.e., movement substantially parallel to longitudinal axis "Y") between sleeve 16 and the cartridge stack ceases. The interlocking engagement of button 28 within aperture 16f serves as a locking mechanism for securing all of the cartridges 18 within sleeve 16 and for securing first cartridge 18A in a position ready for use. Base 22 of first cartridge 18A is retained within bore 16c but mounting member 24 and cleaning tip 26 of first cartridge 18A extend upwardly and outwardly beyond first end 16b of sleeve 16. In this position, first cartridge 18A is ready for use. The remaining cartridges 18B-18E in the stack of cartridges are all retained with bore 16d of sleeve 16. Cover 20 may be inserted into second opening 16c' to seal off this second opening 16c'. Cover 20 is applied in order to keep bore 16d and all the cartridges 18B-18E housed therein in a sanitary state.

As indicated previously herein, dental implement 10 also includes a protective cap 14. Cap 14 is configured to be engaged with sleeve 16 and to surround and protect those portions of first cartridge 18A that extend outwardly beyond first end 16b of sleeve 16. Cap 14 is of shape and size that is complementary in cross-section to sleeve 16. As illustrated herein, that means that cap 14 is generally circular in cross-section and includes a cylindrical wall 14a with a first end 14b and a second end 14c. A bore (not shown) is defined by wall 14a and this bore is of a diameter that is slightly larger than the external diameter of wall 16a of sleeve 16. An opening to the cap's bore is defined in second end 14c of cap 14. An upper region of wall 14a may taper in diameter towards first end 14b. This tapering bore may aid in ensuring that first end 16b of sleeve 16 can only extend upwardly into the cap's bore to a certain extent. The inwardly tapering wall that defines cap 14 therefore acts as a stop, limiting the inward movement of sleeve 16. The movement of sleeve 16 within the cap's bore is halted at a point where a gap exists between first end 16b of sleeve and the inner surface of first end 14b of cap 14. Cleaning tip 26 is of such a length "L" that when engaged with sleeve 16 and inserted into the cap's bore, cleaning tip 26 will not contact the interior surface of cap 14 when sleeve 16 is inserted to the greatest degree possible into cap 14. In this way, cap 14 is able to protect cleaning tip 26 and keep the tip sanitary without directly coming into contact with the same.

A clipping member 14d (FIG. 2) extends outwardly and downwardly from an exterior surface of wall 14a and for a distance beyond second end 14c. When cap 14 is engaged with housing assembly 12, the clipping member 14d may angle inwardly toward the exterior surface of wall 16a of sleeve 16 in much the same way as a cap on a pen extends toward the outer surface of the pen when the cap is engaged with the pen. Clipping member 14d may be useful for securing dental implement 10 to any of a number of articles including a shirt pocket, jacket pocket or a pocket or strap in a purse for example. (Cap 14 and sleeve 16 may be positioned such that a region of the pocket or strap on the article becomes clamped between clipping member 14d and the exterior surface of wall 16a.). Whether dental implement 10 is clipped to an article is simply retained loosely in a pocket or purse, for example, a user is able to take dental implement 10 with them wherever they go and use the same when desired. It should be noted that cap 14 is shaped, sized and positioned so that it will not interfere with the locking mechanism (button 28 with aperture 16o) of first cartridge 18A when cap 14 is engaged with sleeve 16.

FIGS. 1 and 2 show that cap 14 may define a plurality of slots 14e in first end 14b. Slot 14e may allow air to flow into the cap's bore and thereby around cleaning tip 26. If cleaning tip 26 has been used and cap 14 has been replaced onto sleeve 16, this air flowing through slots 14e will tend to allow bristles 26b to dry and thereby aid in preventing unsanitary conditions from developing in dental implement 10. It should be noted that it is contemplated that each cartridge 18 will only be used once by a user but it may not be convenient for the user to remove first cartridge 18A from dental implement 10 immediately after use. The removal of a used first cartridge 18A may have to wait until later and so air circulation within the cap's bore is then desirable to dry off bristles 26b.

When a user wishes to use dental implement 10 the user will remove protective cap 14 off first end 16b of sleeve 16. The terminal end 26c (FIG. 16) of cleaning tip 26 that extends outwardly from first end 16b of sleeve 16 is ready for use. The user will grasp sleeve 16 and will position terminal end 26c so that end 26c is able to be inserted into an interproximal space in the user's mouth. Holding onto sleeve 16, the user will move sleeve 16 back and forth (or in and out), up and down and will position sleeve 16 at an angle relative to the user's teeth. In other words, the user may manipulate the position of cleaning tip 26 relative to the user's teeth until they are satisfied the interproximal surfaces of their teeth have had accumulated food debris scraped therefrom. If desired and if possible, the user may rinse off cleaning tip 26 and replace cap 14.

If the user determines it is time to dispose of first cartridge 18A, the user will push inwardly on button 28 of first cartridge 18A in the direction of arrow "A" (FIG. 18) and will simultaneously push the button 28 upwardly in the direction of arrow "B" This motion will cause face 28a of button 28 to be depressed inwardly and to slide back into bore 16d of sleeve 16. The upward movement will ensure that button 28 of first cartridge 18A no longer aligns with aperture 16f.

As first cartridge 18A moves upwardly in the direction of arrow "B", the interlocking engagement of first cartridge 18A and second cartridge 18B (through receipt of the first end 16b of second cartridge 18B in gap 26e of first cartridge 18A) will result in second cartridge 18B being pulled upwardly within bore 16d. Because of the interlocking engagement of second cartridge 18B with third cartridge 18C, and the interlocking engagement of third and fourth cartridges 18C, 18D; and the interlocking engagement of fourth and fifth cartridges 18D, 18E, the movement of first cartridge 18A causes the rest of the stack of cartridges 18B-18E to move upwardly through bore 16d. This is illustrated in FIGS. 18 and 19. The user may grasp that portion of first cartridge 18A that extends outwardly from sleeve 16 and pull the same in the direction of arrow "B" to completely withdraw first cartridge 18A from bore 16d (FIG. 19). As soon as button 28 on second cartridge 18B aligns with aperture 16f, button 28 returns to its non-compressed state and locks second cartridge 18B in place within sleeve 16. The cleaning tip 26 of the second cartridge 18B is then positioned for use. First cartridge 18A may be detached from second cartridge 18B by moving first cartridge 18A out of alignment with longitudinal axis "Y" of sleeve. This can be done by moving first cartridge 18A in the direction of either arrow "D" in FIG. 16. This will break the interlocking engagement between first and second cartridges 18A and 18B.

Figure 20:
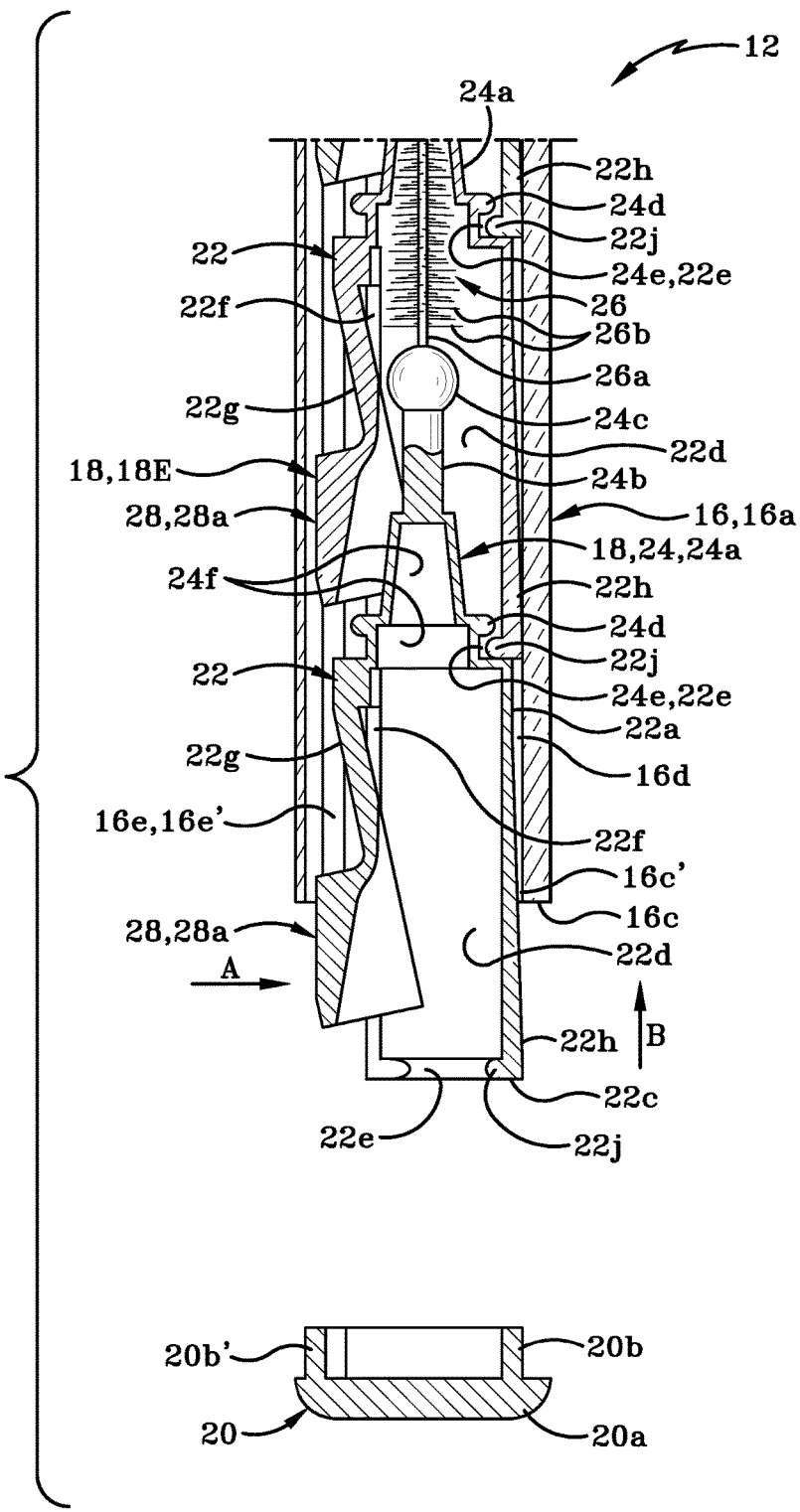
FIG. 20 is a longitudinal cross-section of the second region of the housing assembly as shown in FIG. 17 showing the previously disengaged first cartridge being inserted through the second opening in the sleeve and into a bore of the sleeve of the housing assembly.

Detached first cartridge 18A may be thrown away at this point. Alternatively, first cartridge 18A, which is now what may be referred to as a "spent cartridge", may be reinserted into bore 16d of sleeve. This insertion of the spent first cartridge 18A is illustrated in FIG. 20. The insertion is accomplished by disengaging cover 20 from second end 16c of sleeve 16 and pushing spent first cartridge 18A into bore (after aligning arm 22g and button 28 with channel 16e) and then pushing upwardly in the direction of arrow "B". When face 28a of button 28 of spent first cartridge 18A engages second end 16c of sleeve 16, the button 28 is depressed inwardly in the direction of arrow "A" and slides into bore 16d. Continued upwardly movement of spent first cartridge 18A will cause spent first cartridge 18A to engage fifth cartridge 18E. Spent first cartridge 18A will become snap-fittingly engaged with fifth cartridge 18E and continued pushing upwardly on second end 22c of spent first cartridge 18A will move the same completely into bore 16d, forcing the stack of columns above spent first cartridge 18A upward through bore 16d. This is particularly helpful to ensure that interlocking engagement between all of the cartridges 18A-18E is maintained. Once spent first cartridge is entirely retained within bore 16d, cover 20 may be re-engaged with second end 16c of sleeve 16.

Figure 21:
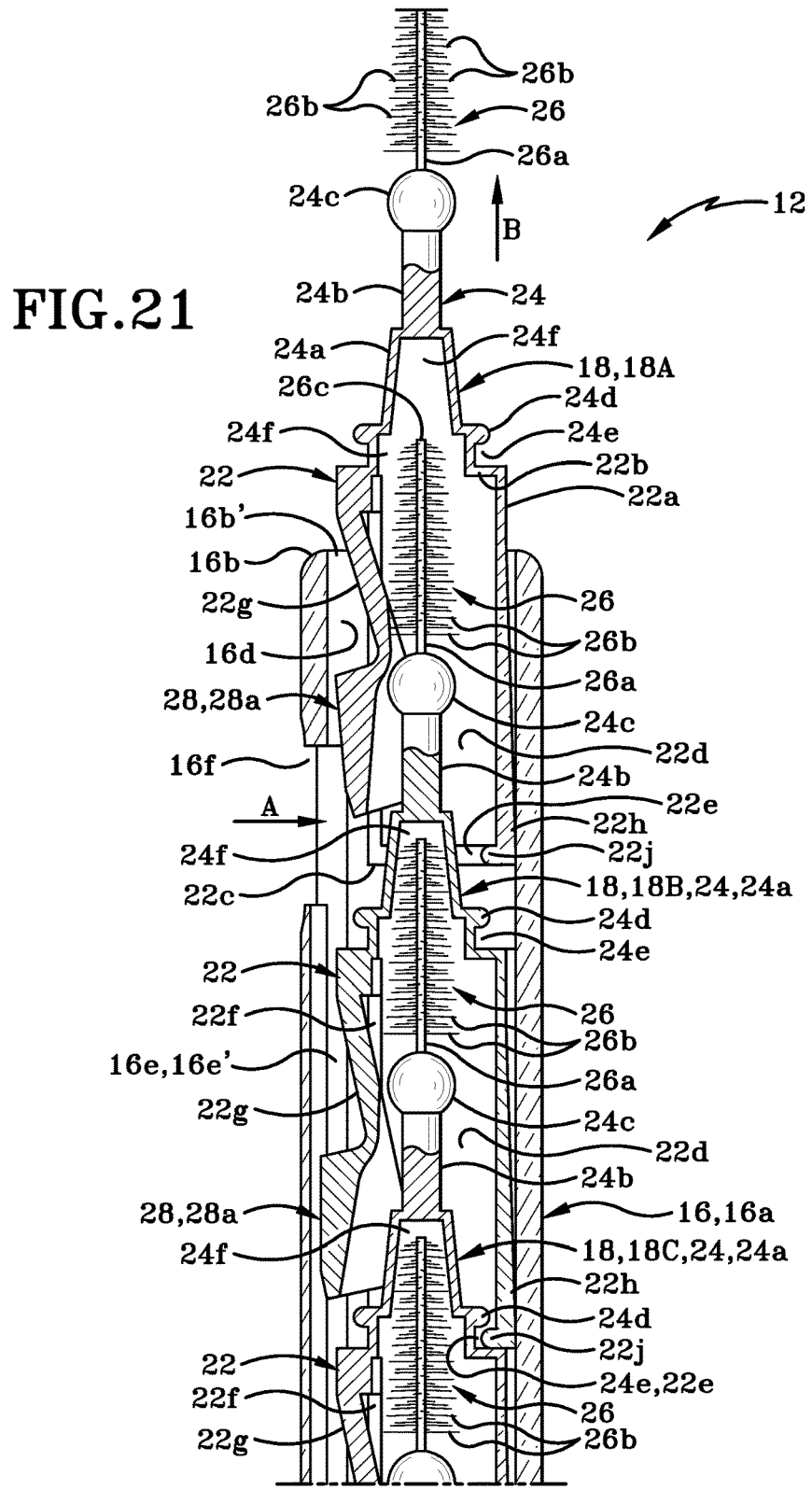
FIG. 21 is a longitudinal cross-section of the first region of the housing assembly showing a second method of removing the first cartridge; said figure illustrating the first cartridge with the button depressed inwardly and the first cartridge being removed from the sleeve but with the second cartridge disengaged from the first cartridge and remaining unmoved within the sleeve's bore.
Figure 22:
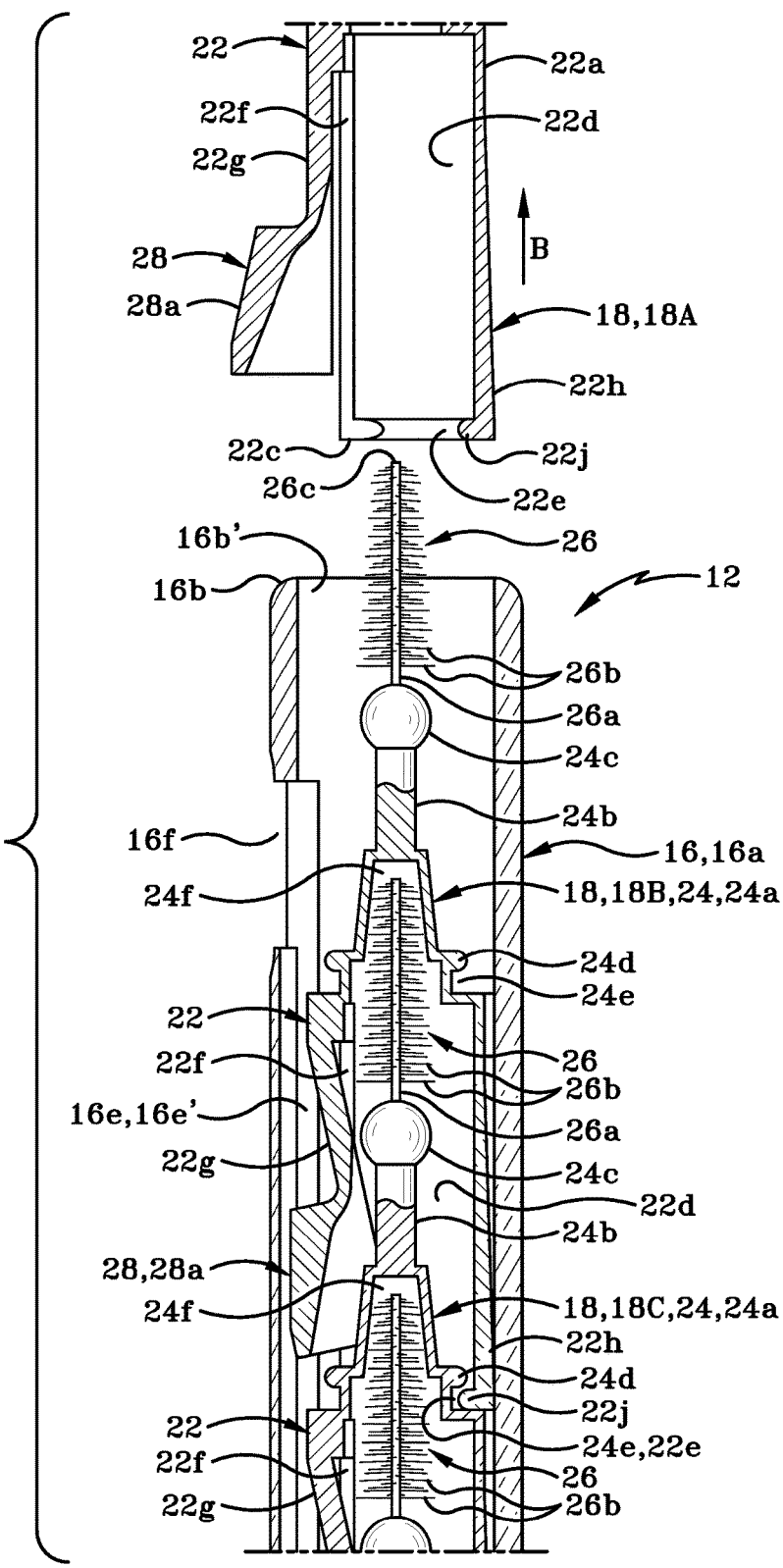
FIG. 22 is a longitudinal cross-section of the first region of the housing assembly as shown in FIG. 21 showing the first cartridge removed from the sleeve and the second cartridge remaining unmoved with the sleeve's bore.
Figure 23:
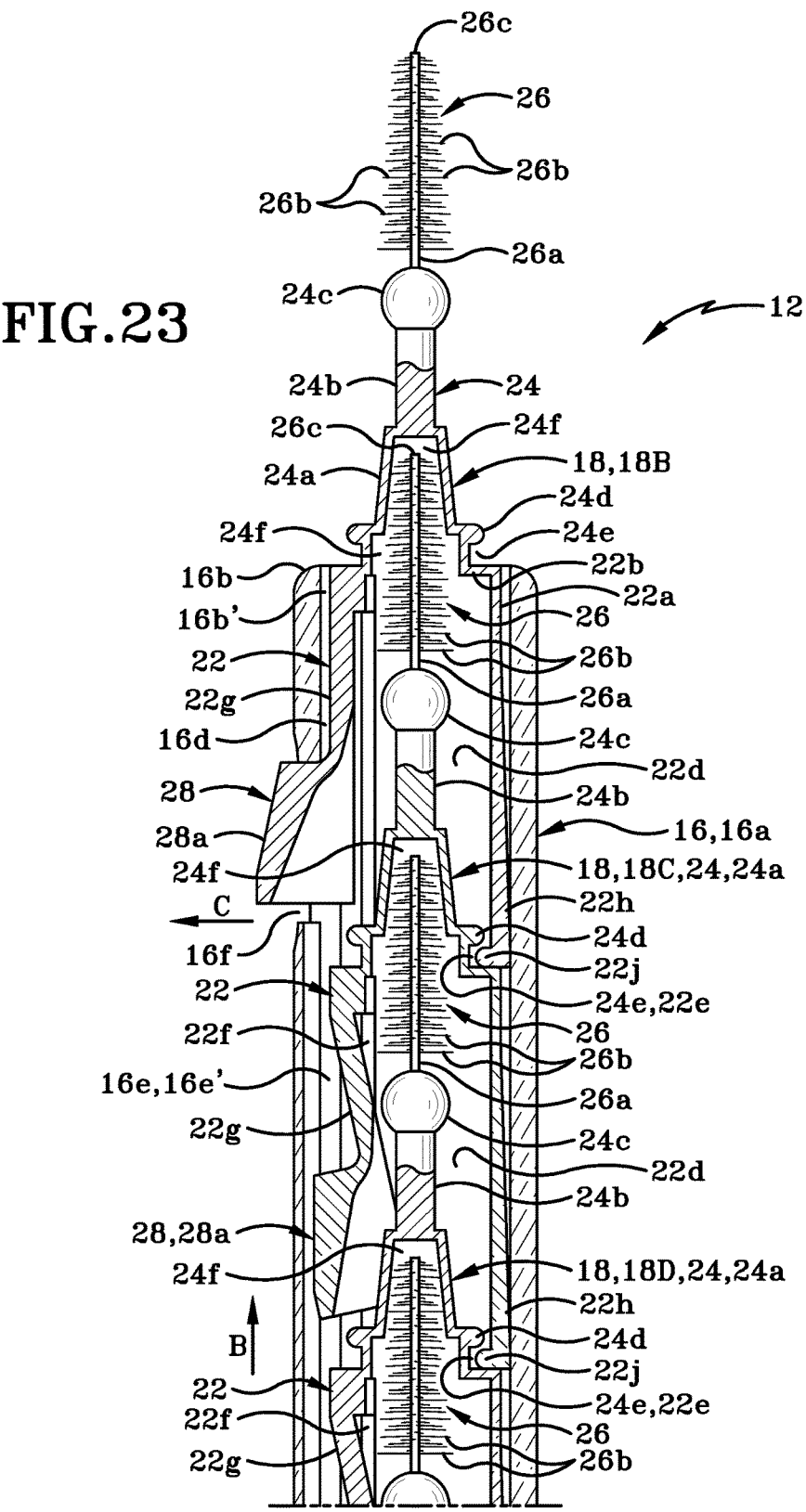
FIG. 23 is a longitudinal cross-section of the first region of the housing assembly showing the stack of cartridges being moved upwardly through the sleeve's bore after insertion of a spent cartridge into the bore of the sleeve as illustrated in FIG. 20.
Figure 24:
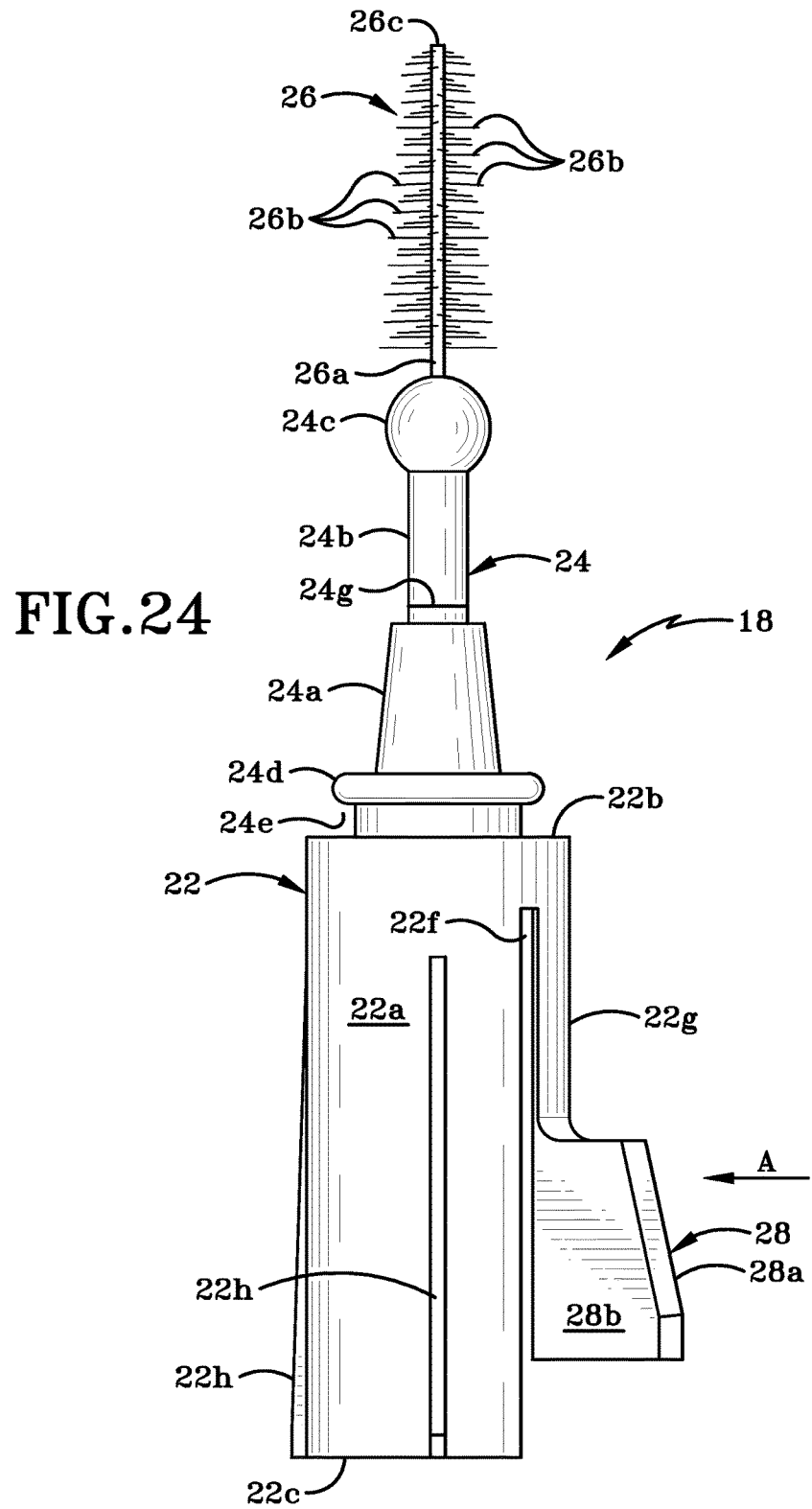
FIG. 24 is an enlarged left side elevation of a second embodiment of a single cartridge that includes a line of weakness for selectively removing the cleaning tip from the cartridge.

FIGS. 21 and 22 show a second method of removing first cartridge 18A from sleeve 16. In this second method, button 28 on first cartridge 18A is depressed inwardly in the direction of arrow "A" and button 28 is additionally pushed in the direction of arrow "B" to slide first cartridge 18A upwardly within bore 16d. First cartridge 18A may break free of its engagement with second cartridge 18B or, in some instances, while a cartridge stack 18A-18E is loaded into sleeve 16 there is no interlocking engagement between adjacent cartridges in the stack. So, when first cartridge 18A is moved upwardly in the direction of arrow "B", second cartridge 18B remains in an unmoved position within bore 16d and does not move upwardly in the direction of arrow "B" with first cartridge 18A. Once first cartridge 18A clears first end 16b of sleeve 16, this spent first cartridge 18A may be reinserted through the second opening at the second end 16c of sleeve 16 in the manner illustrated in FIG. 20. The insertion of spent cartridge 18A causes the stack of cartridges 18B-18E to be moved upwardly within bore 16d and towards first end 16b of sleeve 16. When button 28 of second cartridge 18B aligns with aperture 16f, the force on button 28 is released and button 28 moves outwardly through aperture 16f and locks second cartridge 18B in a position suitable for use.

In other instances, each cartridge 18A-18E may be provided with an annular line of weakness 24g, such as the line of weakness 24g (FIG. 24) that allows cleaning tip 26 and some or all of mounting member 24 to be snapped off first cartridge 18A. The annular line of weakness 24g may be provided at substantially any location along mounting member 24. The snapping off of the cleaning tip 26 may be undertaken by moving grasping the cleaning tip 26 and moving the tip out of alignment with longitudinal axis "Y". When a user wishes to dispose of the cleaning tip 26 and not the whole spent cartridge, the user may grasp cleaning tip 26 between their thumb and first finger and move the grasped portion back and forth in the directions indicated by arrows "D". The cleaning tip 26 will separate from base 22 along line of weakness 24g and can then be discarded. The user may then eject or pull the rest of the first cartridge 18A from sleeve 16. This may be accomplished by the user pushing face 28a of arm 22g inwardly in the direction of arrow "A" and simultaneously pushing arm upwardly toward first end 16b of sleeve 16 in the direction of arrow "B". This motion will slide arm 22g back into bore 16d of sleeve 16 and the interior surface of the sleeve's wall 16a will keep arm compressed within bore 16d. The spent first cartridge 18A will slide out of the first opening 16b' in first end 16b of sleeve 16 and may be discarded or re-inserted into second end 16c of sleeve 16 (shown in FIG. 20) even though cleaning tip 26 has been detached. It should be noted that the cleaning tip 26 may be snapped off from base 22 of spent first cartridge 18 after the cartridge 18A has been removed from sleeve 16 instead of while the cartridge 18A is still within bore 16d.

Figure 25:
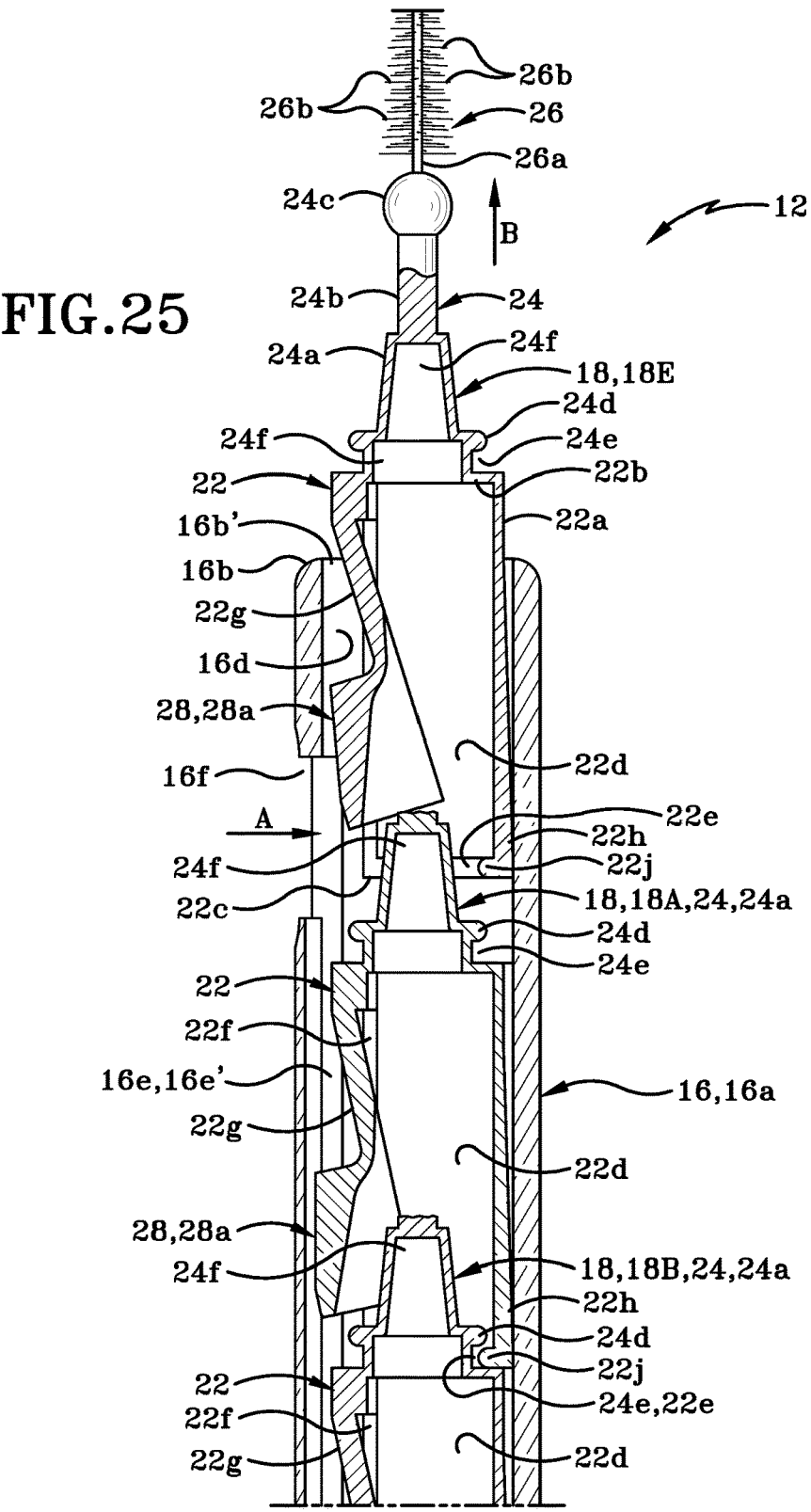
FIG. 25 is a longitudinal cross-section of the first region of the housing assembly showing the cartridges being progressively moved upwardly along the bore of the housing assembly and showing a cartridge with the cleaning tip removed located within the stack of cartridges in the sleeve's bore.
Figure 26:
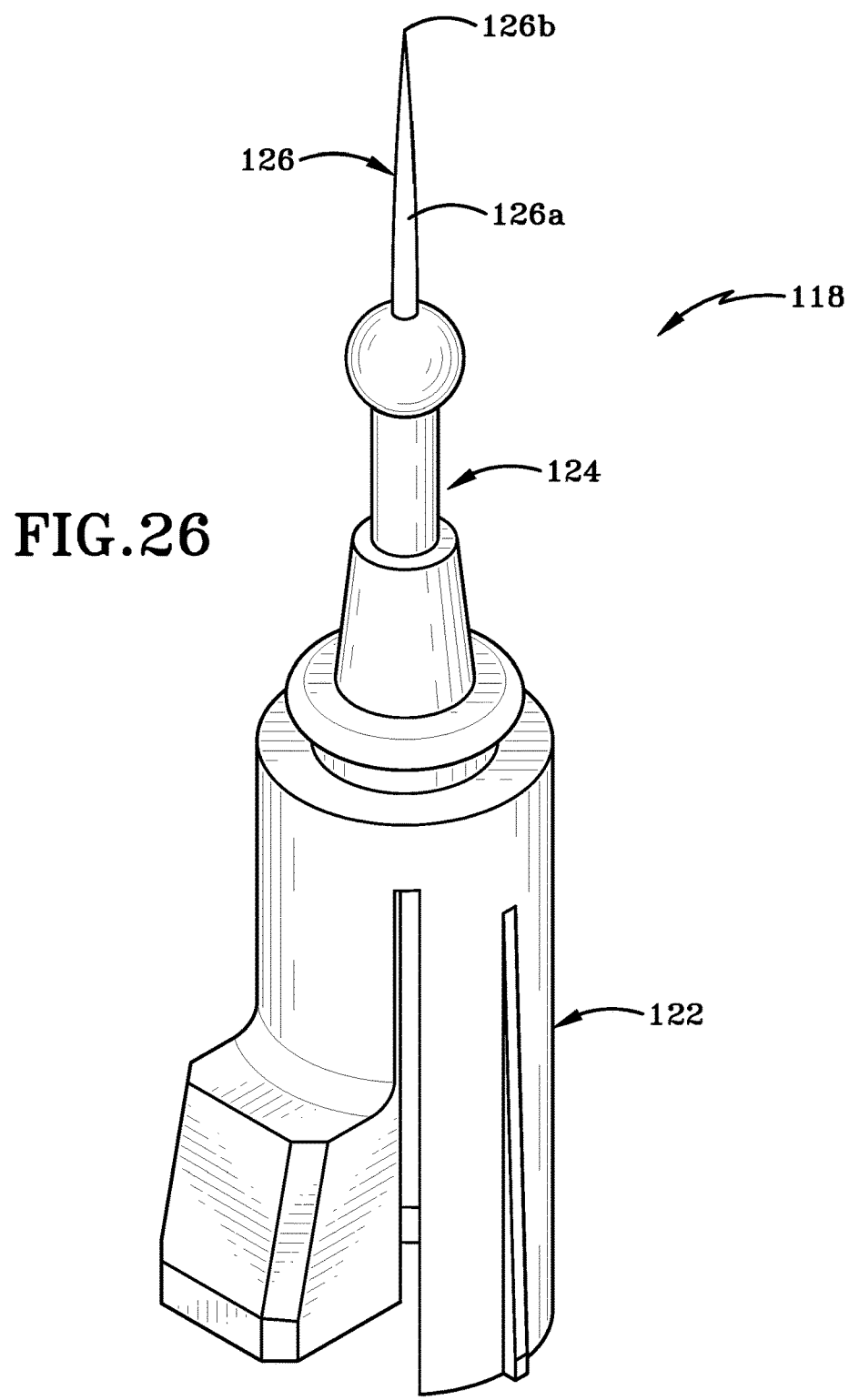
FIG. 26 is an isometric perspective view of a second embodiment of a single cartridge from use in the housing assembly.

FIG. 25 shows the first region of sleeve 16 with fifth cartridge 18E positioned for use and first and second cartridges 18A, 18B located within bore 16d beneath fifth cartridge 18E. Both of the first and second cartridges 18A, 18B are illustrated as having had their cleaning tips 26 detached therefrom prior to reinsertion of the cartridges into bore 16d.

It should be noted that the space vacated by a spent cartridge being removed from the first region of sleeve 16 (spent first cartridge 18A, for example), is substantially of the same size as the space that is occupied by reintroducing spent first cartridge 18A into the bore 16d. Thus, pushing spent first cartridge 18A upwardly through bore 16d and towards first end 16b of sleeve 16 will cause second cartridge 18B to be moved into the correct position for subsequent use.

The procedure of using the cartridge that extends outwardly from the first end 16b of sleeve 16, removing of that used and therefore spent cartridge from the sleeve, (and possibly reinserting the spent cartridge into the bore 16d of sleeve) and subsequent movement of the remaining stacked cartridges through bore 16d will eventually result in the fifth cartridge 18E being moved into a position where the fifth cartridge 18E is ready for use. When the fifth cartridge 18E is reaches a position proximate first end 16b of sleeve 16, it is helpful if the user realizes this is the last unused cartridge from the original stack of cartridges. This is easy to determine if the cleaning tip 26 has been disengaged from first cartridge 18A as discussed above. However, if cleaning tip 26 has not been previously detached from first cartridge 18A there could be a risk that a user could unintentionally use a previously debris-contaminated cleaning tip on first cartridge 18A. In order to try and prevent this from happening, fifth cartridge 18E may be fabricated so that it is of a completely different color relative to the first to fourth cartridges 18A-18D. As soon as the user sees the differently colored cartridge 18E, he or she will know the last clean and used cartridge in the stack of cartridges is extending from the first end 16b of sleeve 16 and they will know that after the use of that differently colored cartridge a new stack of cartridges will have to be inserted into sleeve.

If used cartridges 18A-18D have been discarded immediately after use, then, when the fifth cartridge is used and removed, it will be obvious to the user that there is no longer a cartridge available for use and they will know to load a new stack of cartridges into sleeve 16.

If all cartridges 18A-18E have been used, sleeve 16 may be thrown away or, alternatively and preferably, a completely new stack of cartridges 18A-18E may be loaded into sleeve 16. This is done by inserting the new first cartridge 18A of that new stack through the second opening 16c' in second end 16c of sleeve 16 and pushing the new stack through bore 16d in the direction of arrow "B". As the new stack 18A-18E moves through bore 16d, the successive remnant cartridges of the previous stack of cartridges 18A-18E, if still present, may be progressively removed from sleeve 16 and thrown away.

It will be understood that dental implement 10 may be sold in multiples in a package. So for example, five or ten substantially identical dental implements 10 may be wrapped together for sale. Each dental implement 10 may be fabricated from a differently colored transparent plastic. Each dental implement 10 contained in this package of dental implements may have cartridges 18 that all have identical cleaning tips 26 thereon. Alternatively, cartridges 18 with different cleaning tips 26 may be provided in each of the dental implements within the single package. So, for example, three dental implements may include cartridges 18 having cleaning tips 26 in the form of small interproximal brushes; one dental implement may include cartridges 18 with cleaning tips 26 that have gum stimulator's thereon. All of the interproximal brushes used may have wires 32 and bristles 34 of the same length. On the other hand, some of the interproximal brushes used in cleaning tips 26 on certain cartridges 18 may have different length wires and different patterns, numbers or lengths of bristles.

As was previously alluded to herein, replacement cartridges 18 may be sold separately from dental implements 10. Thus, a user may purchase one or more dental implements 10 that are pre-loaded with one set of cartridges 18 plus an additional package that includes several replacement sets of cartridges 18 therein. The additional cartridges 18 preferably could be sold in a pre-stacked column, such as in FIG. 5, where the column is shrink-wrapped or otherwise packaged. It should be noted that each pre-stacked column of cartridges, 18A-18E (FIG. 13) may include a colored fifth cartridge 18E. For example, this cartridge 18E may be red in color to alert a user to the fact that this is the final cartridge that includes a functioning cleaning tip 26.

Instead of cartridges 18 being moved from proximate second end 16c of sleeve 16 toward first end 16b thereof by the insertion of spent bases 22 into the opening 16c' at second end 16c, dental implement 10 may alternatively be provided with any other type of control mechanism for advancing the cartridges 18 through bore 16d of sleeve 16. For instance, a spring type mechanism may be provided between cover 20 and the fifth cartridge 18E (FIG. 13). A spring in this mechanism may be placed under compression when cover is engaged with sleeve. When first cartridge 18A is removed from sleeve 16 then the spring will start returning to its uncompressed state, thereby urging the column of nested cartridges 18B-18E upwardly toward first end 16b of sleeve 16.

Alternatively, a longitudinally oriented slot may be defined in wall 16a of sleeve 16; where this slot originates in second end 16c of sleeve 16 and terminates in aperture 16f. The slot may be narrower in width than is aperture 16f. Buttons 28 on cartridges 18 may include a narrow neck that extends through this longitudinally oriented slot so that all of the buttons 28 are located outwardly from the exterior surface of wall 16a of sleeve. The user may simply push the button on a lower cartridge upwardly towards the first end 16b of sleeve 16 in order to move one or more cartridges 18 through bore 16d as needed.

Still further, a lever-type mechanism may be provided on wall 16a this lever mechanism may extend through a longitudinal slot as described above that originates in the second end 16c and terminates in, above or below aperture. The lever-type mechanism may be selectively positionable under the second end 22c of any of the cartridges, such as the last cartridge 18E. When the first cartridge 18A is removed from sleeve 16, the lever-type mechanism may be engaged to push the column of nested cartridges 18 through bore 16d. Obviously, this type of system could be utilized to engage any one of the cartridges 18 within sleeve 16 and to move same along bore 16d.

To summarize, housing assembly 12 includes one or more cartridges 18, preferably five cartridges 18, within bore 16d of sleeve 16. Each cartridge 18 is positionable in a predetermined orientation within bore 16d and is configured to selectively move or be moved along bore 16d from proximate second end 16c of housing to proximate first end 16b. Cartridges 18 are in an end-to-end nested arrangement within bore 16d and are advanced therealong by any of the methods set out above or by any other suitable method that will move one or more cartridges through bore 16d to a position where the uppermost cartridge in sleeve 16 is locked into a position where the cleaning tip 26 thereon is ready for use.

The dental implement 10 as disclosed herein is therefore able to be easily carried, used, stored and reloaded with a replacement stack of unused cartridges in a hygienic and effective manner. Because of the external appearance of being a pen, to the casual observer, it is not immediately evident that the user is carrying a dental implement. Because of the relatively elongated sleeve 16, the dental implement 10 is easier for older people, young children and everyone in-between to grasp implement 10 in their hand and to manipulate cleaning tip 26 thereon to clean between their teeth. Additionally, because the dental implement 10 includes a slender sleeve 16 and even narrower cleaning tip 26, the disclosed dental implement 10 is easily inserted and manipulated within the user's mouth. The device is far simpler to hold than miniature flossing wands and does not require the almost full insertion of the user's hand into the mouth—as is the case with floss threads.

In some instances, it may be desirable for dental implement 10 to be a single use component. In these instances, after a series of cartridges 18 have been inserted into bore 16d of sleeve 16, cover 20 is bonded to second end 16c of wall 16a of sleeve 16 so that the second opening 16c' to bore 16d is closed off. Access to bore 16d through that second end 16c' of sleeve 16 is thereby substantially permanently prevented. When all of the cartridges 18 have been progressively utilized and disposed of, sleeve 16 and cap 14 may also be thrown away.

FIGS. 26 and 27 show a second embodiment and a third embodiment of a cartridge that has a differently configured cleaning tip thereon. FIG. 26 illustrates a cartridge 118 having a base 122, a mounting member 124, and a cleaning tip 126. Base 122 and mounting member 124 are substantially similar in shape and function to base 22 and mounting member 24, respectively. Cleaning tip 126 differs from cleaning tip 26. Cleaning tip 126 may be molded as part of mounting member 124 or may have a first end that is embedded within mounting member 124 and extends outwardly therefrom. Cleaning tip 126 includes an elongate tapering member 126a that has an apex 126b and is suitable for use as a toothpick.

FIG. 27 illustrates a cartridge 218 having a base 222, a mounting member 224, and a cleaning tip 226. Base 222 and mounting member 224 are substantially similar in shape and function to base 22 and mounting member 24, respectively. Cleaning tip 226 differs from cleaning tip 26. Cleaning tip 226 may be molded as part of mounting member 224 or may have a first end that is embedded within mounting member 224 and extends outwardly therefrom. Cleaning tip 226 is illustrated as including a conical member 226 that has a bottom region that is substantially of the same width as bulbous second region 224c of mounting member 224. Conical member 226 tapers gradually to a tip 226b. Conical member 226 may be fabricated from a somewhat flexible rubber and be useful as a gum stimulator. Any of the cleaning tips disclosed herein and any others that are provided in a dental implement such as the implement disclosed herein will be invaluable to all people including orthodontic patients.

It will be understood that any other desired cleaning tip may be incorporated into a cartridge for engagement with sleeve 16.

While the cartridges 18, 118, 218 have been illustrated and described herein of being of a particular configuration and use, it will be understood that the exact shape, size and proportions of various component parts of these cartridges may be varied or omitted without departing from the scope of the invention. So, for example, instead of the cleaning tip 26 comprising a first region 24a, a shaft 24b and a frusto-conical second region 24c, a single shaft of substantially constant diameter may extend outwardly from first end 22b of base 22. Other variations in the shape of base 22, shaft 24 or of cleaning tip 26 may be utilized.

It will be understood that while the attached interproximal brush has been disclosed as being fabricated using an embedded wire member and bristles that are engaged therewith, any other type of brush or flossing device, no matter the manner in which they are fabricated, may be utilized in cartridges 18.

It will further be understood that the brush or flossing device may extend directly out of the first end 22b of base 22; i.e., mounting member 24 may be omitted from dental implement 10.

It has been disclosed herein that the cartridges 18 are locked in a fixed position relative to sleeve 16 by way of engaging a locking member 22g/28 on sleeve 16 with an aperture 16f on the sleeve. It will be understood that these two components that provide the locking engagement between sleeve 16 and cartridges 18 may be reverse. In other words, the aperture may be provided on the cartridge and the movable locking member, similar to arm 22g and button 28 may be provided on the sleeve 18. It will be understood that any suitable way of detachably securing the cartridges to the sleeve may be utilized. The interlocking aperture 16f and spring-loaded arm 22g, 28 are provided as an example of one suitable way of making this interlocking engagement between the cartridge and sleeve.

It may be understood that cover 20 may be omitted and that opening 16c" may be accessible at all times for insertion of spent cartridge 18, if it is desired by the user to insert such cartridges. Whether cover 20 is provided or not, if for some reason the stack of cartridges 18 does not advance through bore 16 when the uppermost cartridge, such as cartridge 18A, is removed from sleeve 16, an unrelated article, such as a pen tip, may be used to push on the second end 22c of the lowermost cartridge (such as 18E). Pushing on second end 22c with this article will cause the stack of cartridges to move upwardly until the next unused cartridge's button 28 aligns with aperture 16f and moves therethrough, locking that next unused cartridge in a position where the cleaning tip 26 thereon extends outwardly from first end 16b of sleeve 16.

It will also be understood that instead of ribs 22h being on base 22, they may be provided on the interior surface of base 22 that defines bore 22d and the exterior surface of base 22 may be smooth.

In the foregoing description, certain terms have been used for brevity, clearness, and understanding. No unnecessary limitations are to be implied therefrom beyond the requirement of the prior art because such terms are used for descriptive purposes and are intended to be broadly construed. Moreover, the description and illustration set out herein are an example not limited to the exact details shown or described.

The invention claimed is:

1. A dental implement comprising:
a sleeve having a wall with a first end and a second end; said sleeve defining a bore that extends between the first and second ends; and
a plurality of cartridges received within the bore and movable therealong from the second end to the first end of the sleeve; wherein each of the plurality of cartridges is provided with a single cleaning tip; and wherein the plurality of cartridges includes a first cartridge; and wherein the first cartridge is selectively positioned within the bore such that the first cleaning tip of the first cartridge extends outwardly beyond the first end of the sleeve.

2. The dental implement as defined in claim 1, further comprising a cap that is selectively engageable with the first end of the sleeve to cover the first cleaning tip.

3. The dental implement as defined in claim 1, wherein each of the plurality of cartridges is a single use cartridge.

4. The dental implement as defined in claim 1, each of the plurality of cartridges is disposable.

5. The dental implement as defined in claim 1, wherein cleaning tip is of the first cartridge a bristled brush.

6. The dental implement as defined in claim 1, wherein each of the plurality of cartridges includes a locking member that selectively locks the cartridge in a fixed position within the sleeve's bore.

7. The dental implement as defined in claim 6, wherein the wall of the sleeve defines an aperture therein and the locking member selectively extends through the aperture to lock the cartridge in the fixed position within the bore.

8. The dental implement as defined in claim 6, wherein the locking member comprises an arm provided on the cartridge and the arm is movable between a first position and a second position; and when the arm is in the first position the cartridge is movable along the sleeve's bore; and when the arm is in the second position the cartridge is retained in the fixed position within the sleeve's bore.

9. The dental implement as defined in claim 1, wherein the plurality of cartridges includes one or more additional cartridges that are retained within the bore and are movable within the bore and when the first cartridge has been removed from the bore one of the one or more additional cartridges is positionable within the bore so that the cleaning tip on the one of the one or more additional cartridges extends outwardly beyond the first end of the sleeve.

10. The dental implement as defined in claim 9, wherein the first cartridge and the one or more additional cartridges are stackable one on top of the other to form a cartridge stack that is received within the bore of the sleeve.

11. The dental implement as defined in claim 10, wherein the cleaning tips on the plurality of cartridges are all identical.

12. The dental implement as defined in claim 10, wherein the cleaning tips of the plurality of cartridges are different from each other.

13. A method of cleaning an interproximal space in a person's mouth; said method including:
providing a dental implement comprising a sleeve having a wall with a first end, a second end, and a bore defined between the first and second ends; and a plurality of cartridges received within the bore and movable therealong from the second end of the sleeve to the first end of the sleeve; wherein each of the plurality of cartridges is provided with a cleaning tip; and wherein the plurality of cartridges includes a first cartridge movable along the sleeve's bore of the sleeve; wherein the first cartridge includes a first cleaning tip;
selectively moving the first cartridge along the bore to a position proximate the first end of the sleeve;
extending the first cleaning tip on the first cartridge outwardly beyond the first end of the sleeve; and
using the first cleaning tip in a person's mouth.

14. The method as defined in claim 13, wherein the step of using the first cleaning tip comprises:
inserting the first cleaning tip into the interproximal space in the person's mouth; and
moving the first cleaning tip back-and-forth, up-and-down; and from side-to-side between the teeth bounding the interproximal space.

15. The method as defined in claim 14, further comprising:
engaging a locking member; and
locking the first cartridge proximate the first end of the sleeve utilizing the locking member.

16. The method as defined in claim 15, further comprising:
arranging the plurality of cartridges one on top of the other to form a cartridge stack;
inserting the cartridge stack into an opening in the second end of the sleeve; and wherein the first cartridge comprises an uppermost cartridge in the cartridge stack; and
moving the cartridge stack upwardly through the bore of the sleeve and towards the first end when the first cartridge is moved in the bore.

17. The method as defined in claim 16, further comprising;
inserting the removed first cartridge through the opening in the second end of the bore;
engaging the inserted first cartridge with the cartridge stack so that the inserted first cartridge becomes a lowermost cartridge in the cartridge stack.

18. The method as defined in claim 17, further comprising:

breaking the first cleaning tip off the removed first cartridge prior to inserting the first cartridge into the opening in the second end of the bore.

19. The dental implement as defined in claim 1, wherein the plurality of cartridges received within the bore are movable therealong from an opening defined in the second end of the sleeve to an opening defined in the first end of the sleeve.

* * * * *